United States Patent
Jang et al.

(10) Patent No.: US 11,877,510 B2
(45) Date of Patent: *Jan. 16, 2024

(54) HETEROCYCLIC COMPOUND AND ORGANIC LIGHT-EMITTING ELEMENT COMPRISING SAME

(71) Applicant: LG CHEM, LTD., Seoul (KR)

(72) Inventors: Boonjae Jang, Daejeon (KR); Dong Hoon Lee, Daejeon (KR); Dong Uk Heo, Daejeon (KR); Miyeon Han, Daejeon (KR); Minyoung Kang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 269 days.

This patent is subject to a terminal disclaimer.

(21) Appl. No.: 17/064,409

(22) Filed: Oct. 6, 2020

(65) Prior Publication Data
US 2021/0028372 A1    Jan. 28, 2021

Related U.S. Application Data

(60) Continuation of application No. 16/158,171, filed on Oct. 11, 2018, now Pat. No. 10,916,710, and a
(Continued)

(30) Foreign Application Priority Data

| Apr. 4, 2014 | (KR) | ......... | 10-2014-0040818 |
| Feb. 5, 2015 | (KR) | ......... | 10-2015-0017929 |
| Mar. 31, 2015 | (KR) | ......... | 10-2015-0045586 |

(51) Int. Cl.
*H10K 85/60* (2023.01)
*C09K 11/02* (2006.01)
(Continued)

(52) U.S. Cl.
CPC ......... *H10K 85/654* (2023.02); *C07D 251/24* (2013.01); *C09K 11/025* (2013.01);
(Continued)

(58) Field of Classification Search
CPC ............. H01L 51/0067; H01L 51/0052; H01L 51/0054; H01L 51/0055; H01L 51/0058;
(Continued)

(56) References Cited

U.S. PATENT DOCUMENTS

| 6,821,643 | B1 | 11/2004 | Hu et al. |
| 9,502,669 | B2 | 11/2016 | Huh et al. |

(Continued)

FOREIGN PATENT DOCUMENTS

| CN | 1702065 A | 11/2005 |
| CN | 1867646 A | 11/2006 |

(Continued)

OTHER PUBLICATIONS

Kukhta, Nadzeya A., et al. "Effect of linking topology on the properties of star-shaped derivatives of triazine and fluorene." Synthetic metals 195 (2014): 266-275. (Year: 2014).*

(Continued)

*Primary Examiner* — Dawn L Garrett
(74) *Attorney, Agent, or Firm* — Bryan Cave Leighton Paisner LLP

(57) ABSTRACT

The present specification provides a hetero-cyclic compound and an organic light emitting device comprising the same.

14 Claims, 2 Drawing Sheets

Related U.S. Application Data division of application No. 15/301,607, filed as application No. PCT/KR2015/003291 on Apr. 2, 2015, now Pat. No. 10,510,963.

(51) Int. Cl.
| | | |
|---|---|---|
| *C07D 251/24* | (2006.01) | |
| *C09K 11/06* | (2006.01) | |
| *H10K 50/165* | (2023.01) | |
| *H10K 50/17* | (2023.01) | |
| *H10K 85/30* | (2023.01) | |

(52) U.S. Cl.
CPC ............ *C09K 11/06* (2013.01); *H10K 85/615* (2023.02); *H10K 85/622* (2023.02); *H10K 85/623* (2023.02); *H10K 85/626* (2023.02); *H10K 50/165* (2023.02); *H10K 50/171* (2023.02); *H10K 85/30* (2023.02)

(58) Field of Classification Search
CPC ............. H01L 51/0077; H01L 51/5076; H01L 51/5092; H01L 51/5012; H01L 51/5056; H01L 51/5072; C07D 251/24; C07D 209/82; C07D 251/12; C07D 401/14; C07D 403/14; C09K 11/025; C09K 11/06; H10K 85/654; H10K 85/615; H10K 85/622; H10K 85/623; H10K 85/626; H10K 50/165; H10K 50/171; H10K 85/30

See application file for complete search history.

(56) References Cited

U.S. PATENT DOCUMENTS

| | | | |
|---|---|---|---|
| 9,640,766 B2 * | 5/2017 | Jang | ........................ C09K 11/06 |
| 9,960,363 B2 | 5/2018 | Eum et al. | |
| 10,032,990 B2 | 7/2018 | Lee et al. | |
| 10,381,572 B2 * | 8/2019 | Jang | ........................ C09K 11/025 |
| 10,510,963 B2 * | 12/2019 | Jang | ........................ C09K 11/06 |
| 10,964,892 B2 * | 3/2021 | Huh | ........................ H10K 85/622 |
| 11,271,167 B2 * | 3/2022 | Jang | ........................ C07D 471/04 |
| 11,342,508 B2 * | 5/2022 | Jang | ........................ C07D 251/12 |
| 11,362,280 B2 * | 6/2022 | Jang | ........................ C07F 9/6561 |
| 2003/0165715 A1 | 9/2003 | Yoon et al. | |
| 2003/0170490 A1 | 9/2003 | Hu et al. | |
| 2006/0135766 A1 | 6/2006 | Hayoz et al. | |
| 2007/0190355 A1 | 8/2007 | Ikeda et al. | |
| 2010/0039026 A1 | 2/2010 | Yang et al. | |
| 2011/0037062 A1 | 2/2011 | Fukumatsu et al. | |
| 2011/0095282 A1 | 4/2011 | Pflumm et al. | |
| 2011/0121274 A1 | 5/2011 | Parham et al. | |
| 2011/0215308 A1 | 9/2011 | Irn et al. | |
| 2011/0284831 A1 | 11/2011 | Kaiser et al. | |
| 2012/0126217 A1 | 5/2012 | Yoshida et al. | |
| 2012/0214993 A1 | 8/2012 | Aihara et al. | |
| 2012/0286249 A1 | 11/2012 | Lee et al. | |
| 2014/0061629 A1 | 3/2014 | Murase et al. | |
| 2014/0110694 A1 | 4/2014 | Shin et al. | |
| 2014/0367654 A1 | 12/2014 | Kim et al. | |
| 2015/0144897 A1 | 5/2015 | Kang et al. | |
| 2015/0236273 A1 | 8/2015 | Jang et al. | |
| 2015/0243897 A1 | 8/2015 | Montenegro et al. | |
| 2015/0349270 A1 | 12/2015 | Lee et al. | |
| 2016/0072073 A1 | 3/2016 | Lee et al. | |
| 2016/0093808 A1 | 3/2016 | Adamovich et al. | |
| 2016/0218298 A1 | 7/2016 | Lee et al. | |
| 2017/0005273 A1 | 1/2017 | Hwang et al. | |
| 2017/0104163 A1 | 4/2017 | Lee et al. | |
| 2018/0053900 A1 | 2/2018 | Eum et al. | |

FOREIGN PATENT DOCUMENTS

| | | | |
|---|---|---|---|
| CN | 1934213 A | | 3/2007 |
| CN | 101656301 A | | 2/2010 |
| CN | 101960637 A | | 1/2011 |
| CN | 102077379 A | | 5/2011 |
| CN | 102077384 A | | 5/2011 |
| CN | 102201432 A | | 9/2011 |
| CN | 102292841 A | | 12/2011 |
| CN | 102471320 A | | 5/2012 |
| CN | 105392789 A | | 3/2016 |
| CN | 106471093 A | | 3/2017 |
| EP | 2749560 A1 | | 7/2014 |
| EP | 2752902 A1 | | 7/2014 |
| JP | 2012513668 A | | 6/2012 |
| JP | 2018115125 A | | 7/2018 |
| JP | 2018177668 A | | 11/2018 |
| KR | 10-2011-0111093 A | | 10/2011 |
| KR | 10-2011-0113469 A | | 10/2011 |
| KR | 1020120138673 A | | 12/2012 |
| KR | 10-2013-0115160 A | | 10/2013 |
| KR | 1020130116041 A | | 10/2013 |
| KR | 1020140009919 A | | 1/2014 |
| KR | 10-2015-0002072 | | 1/2015 |
| WO | 2004/077885 | | 9/2004 |
| WO | 2007/029798 A1 | | 3/2007 |
| WO | 2012/150826 A1 | | 11/2012 |
| WO | 2012/173369 A2 | | 12/2012 |
| WO | 2013077352 A1 | | 5/2013 |
| WO | 2013/085243 A1 | | 6/2013 |
| WO | 2013/180503 A1 | | 12/2013 |
| WO | 2014023388 | | 2/2014 |
| WO | 2014185694 A1 | | 11/2014 |
| WO | 2014200148 A1 | | 12/2014 |
| WO | 2015005559 A1 | | 1/2015 |
| WO | 2016/024728 A1 | | 2/2016 |
| WO | 2016/105141 A2 | | 6/2016 |

OTHER PUBLICATIONS

Chen, Hsiao-Fan, et al. "1, 3, 5-Triazine derivatives as new electron transport-type host materials for highly efficient green phosphorescent OLEDs." Journal of Materials Chemistry 19.43 (2009): 8112-8118. (Year: 2009).*

Zhong et al.: "New Conjugated Triazine Based Molecular Materials for Application in Optoelectronic Devices: Design, Synthesis, and Properties", J Phys Chem C 115: 2423-2427 (2010).

Reghu et al.: "Glass forming donor-substituted s-triazines: Photophysical and electrochemical properties", Dyes and Pigments 97: 412-422 (2013).

Ren et al.: "Star-Shaped donor-pi-Acceptor Conjugated Oligomers with 1,3,5-Triazine Cores: Convergent Synthesis and Multifunctional Properties", J Phys Chem B 114: 10374-10383 (2010).

* cited by examiner

HETEROCYCLIC COMPOUND AND ORGANIC LIGHT-EMITTING ELEMENT COMPRISING SAME

CROSS-REFERENCE TO RELATED APPLICATIONS

This application is a Continuation of co-pending U.S. patent application Ser. No. 16/158,171, filed Oct. 11, 2018, which is a Divisional of U.S. patent application Ser. No. 15/301,607, filed Oct. 3, 2016, which issued as U.S. Pat. No. 10,510,963 on Dec. 17, 2019 and which is a National Stage Application of International Application No. PCT/KR2015/003291, filed Apr. 2, 2015, and claims priority to and the benefit of Korean Patent Application No. 10-2014-0040818, filed in the Korean Intellectual Property Office on Apr. 4, 2014, Korean Patent Application No. 10-2015-0017929, filed in the Korean Intellectual Property Office on Feb. 5, 2015, and Korean Patent Application No. 10-2015-0045586, filed in the Korean Intellectual Property Office on Mar. 31, 2015, the contents of which are incorporated herein by reference in their entireties.

TECHNICAL FIELD

The present specification relates to a hetero-cyclic compound and an organic light emitting device comprising the same.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multilayered structure composed of different materials in order to improve the efficiency and stability of an organic light emitting device in many cases, and for example, may be composed of a hole injection layer, a hole transporting layer, a light emitting layer, an electron transporting layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

CITATION LIST

Patent Document

Official Gazette of Korean Patent Application Laid-Open No. 2000-0051826

DISCLOSURE

Technical Problem

The present specification describes a hetero-cyclic compound and an organic light emitting device comprising the same.

Technical Solution

An exemplary embodiment of the present specification provides a compound represented by the following Formula 1:

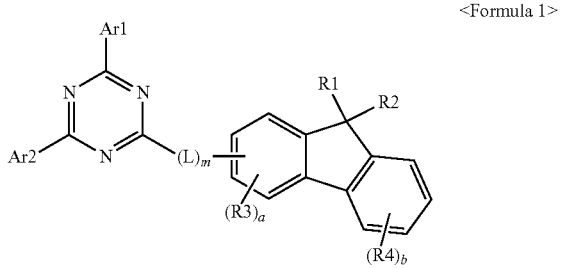

<Formula 1> in Formula 1,
Ar1 and Ar2 are the same as each other, and each is:
a phenyl group, which is unsubstituted or substituted with one or more substituents selected from the group consisting of deuterium, a halogen group, a nitrile group, a nitro group, a hydroxy group, a carbonyl group, an ester group, an imide group, an amino group, a phosphineoxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aralkyl group, an aralkenyl group, an alkylaryl group, an alkylamine group, an aralkylamine group, a heteroarylamine group, an arylamine group, an arylphosphine group, and a hetero-cyclic group;
a biphenyl group, which is unsubstituted or substituted with one or more substituents selected from the group consisting of deuterium, a halogen group, a nitrile group, a nitro group, a hydroxy group, a carbonyl group, an ester group, an imide group, an amino group, a phosphineoxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group;
a naphthyl group, which is unsubstituted or substituted with one or more substituents selected from the group consisting of deuterium, a halogen group, a nitrile group, a nitro group, a hydroxy group, a carbonyl group, an ester group, an imide group, an amino group, a phosphineoxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; or
a phenanthryl group, which is unsubstituted or substituted with one or more substituents selected from the group consisting of deuterium, a halogen group, a nitrile group, a nitro group, a hydroxy group, a carbonyl group, an ester group, an imide group, an amino group, a phosphineoxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group;

L is a substituted or unsubstituted phenylene or a substituted or unsubstituted biphenylylene;

R1 and R2 are the same as or different from each other, and each independently is hydrogen, deuterium, a halogen group, a nitrile group, a nitro group, a hydroxy group, a carbonyl group, an ester group, an imide group, an amino group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group; a substituted or unsubstituted alkylamine group, a substituted or unsubstituted aralkylamine group, a substituted or unsubstituted heteroarylamine group, a substituted or unsubstituted arylamine group, a substituted or unsubstituted arylheteroarylamine group, a substituted or unsubstituted arylphosphine group, a substituted or unsubstituted phosphineoxide group, a substituted or unsubstituted aryl group, or a substituted or unsubstituted hetero-cyclic group, or may combine with an adjacent group to form a substituted or unsubstituted ring;

R3 and R4 are the same as or different from each other, and each independently is hydrogen, deuterium, a halogen group, a nitrile group, a nitro group, a hydroxy group, a carbonyl group, an ester group, an imide group, an amino group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted alkylamine group, a substituted or unsubstituted aralkylamine group, a substituted or unsubstituted arylphosphine group, or a substituted or unsubstituted phosphineoxide group, or may combine with an adjacent group to form a substituted or unsubstituted ring;

m is an integer of 1 to 5;
a is an integer of 0 to 3; and
b is an integer of 0 to 4; and
when m, a, and b are each 2 or more, the structures in the parenthesis are the same as or different from each other.

One embodiment of the present specification provides a compound represented by the following Chemical Formula 1:

<Chemical Formula 1>

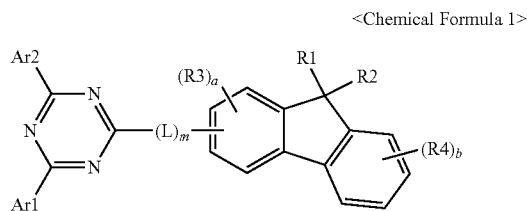

wherein:

R3 is hydrogen, deuterium, a halogen group, a nitrile group, a nitro group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group; a substituted or unsubstituted boron group, a substituted or unsubstituted aryl group, or a substituted or unsubstituted hetero-cyclic group, or adjacent two or more R3s bond to each other to form a monocyclic or polycyclic ring;

R4 is hydrogen, deuterium, a halogen group, a nitrile group, a nitro group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group; a substituted or unsubstituted boron group, a substituted or unsubstituted aryl group, a substituted or unsubstituted monocyclic or dicyclic hetero-cyclic group including one or more of O and S atoms, a substituted or unsubstituted pyrrole group, a substituted or unsubstituted imidazole group, a substituted or unsubstituted triazole group, a substituted or unsubstituted pyridyl group, a substituted or unsubstituted bipyridyl group, a substituted or unsubstituted pyrimidyl group, a substituted or unsubstituted triazole group, a substituted or unsubstituted acridyl group, a substituted or unsubstituted pyridazine group, a substituted or unsubstituted pyrazinyl group, a substituted or unsubstituted quinolinyl group, a substituted or unsubstituted quinazoline group, a substituted or unsubstituted quinoxalinyl group, a substituted or unsubstituted phthalazinyl group, a substituted or unsubstituted pyridopyrimidinyl group, a substituted or unsubstituted pyridopyrazinyl group, a substituted or unsubstituted pyrazinopyrazinyl group, a substituted or unsubstituted isoquinoline group, a substituted or unsubstituted indole group, a substituted or unsubstituted benzimidazole group, or a substituted or unsubstituted phenanthroline group, or adjacent two or more R4s bond to each other to form a monocyclic or polycyclic ring;

R1 and R2 are the same as or different from each other, and each independently is hydrogen, deuterium, a halogen group, a substituted or unsubstituted alkyl group, a substituted or unsubstituted alkoxy group, a substituted or unsubstituted thioalkoxy group, a substituted or unsubstituted cyclic alkyl group, a substituted or unsubstituted alkenyl group, a substituted or unsubstituted alkoxy group, a substituted or unsubstituted thioalkoxy group, a substituted or unsubstituted aryl group, a substituted or unsubstituted hetero-cyclic group, a substituted or unsubstituted aryloxy group, or a substituted or unsubstituted heteroaryloxy group;

Ar1 and Ar2 are the same as or different from each other, and each independently is a substituted or unsubstituted aryl group or a substituted or unsubstituted heteroaryl group;

L is a direct bond, a substituted or unsubstituted arylene, or a substituted or unsubstituted heteroarylene;

a is an integer of 0 to 3;

b is an integer of 0 to 4;

m is an integer of 0 to 5;

when a is 2 or more, the R3s are the same as or different from each other, when b is 2 or more, the R4s are the same as or different from each other, and when m is 2 or more, the Ls are the same as or different from each other.

According to one embodiment of the present specification, Ar1 and Ar2 are the same as or different from each other, and each independently is a substituted or unsubstituted phenyl group, a substituted or unsubstituted naphthyl group, a substituted or unsubstituted biphenyl group, a substituted or unsubstituted terphenyl group, a substituted or unsubstituted anthracenyl group, a substituted or unsubstituted phenanthryl group, a substituted or unsubstituted pyrenyl group, a substituted or unsubstituted perylenyl group, a substituted or unsubstituted chrysenyl group, a substituted or unsubstituted fluorenyl group, or a substituted or unsubstituted heteroaryl group.

According to one embodiment of the present specification, Chemical Formula 1 may be the following Chemical Formula 18:

<Chemical Formula 18>

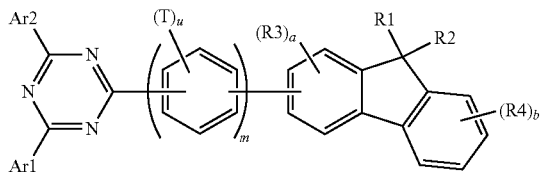

wherein in Chemical Formula 18:

Ar1, Ar2, R1 to R4, m, a and b have the same definitions as in Chemical Formula 1;

T is hydrogen, deuterium, a halogen group, a nitrile group, a nitro group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted aryl group, or a substituted or unsubstituted heterocyclic group, or adjacent two or more Ts bond to each other to form a monocyclic or polycyclic ring; and u is an integer of 0 to 4, and when u is 2 or more, Ts are the same as or different from each other.

Further, an exemplary embodiment of the present specification provides: an organic light emitting device including: a first electrode; a second electrode provided to face the first electrode; and one or more organic material layers provided between the first electrode and the second electrode, in which one or more of the organic material layers include the compound of Formula 1.

Advantageous Effects

The compound described in the present specification may be used as a material for the organic material layer of the organic light emitting device. The compound according to at least one exemplary embodiment may improve the efficiency and improve low driving voltage and/or service life characteristics in the organic light emitting device. In particular, the compound described in the present specification may be used as a material for hole injection, hole transport, hole injection and hole transport, light emission, electron transport, or electron injection. In addition, the compound described in the present specification may be used preferably as a material for a light emitting layer, electron transport, or electron injection, and more preferably as a material for electron transport or electron injection.

MODE FOR INVENTION

Figure 1:
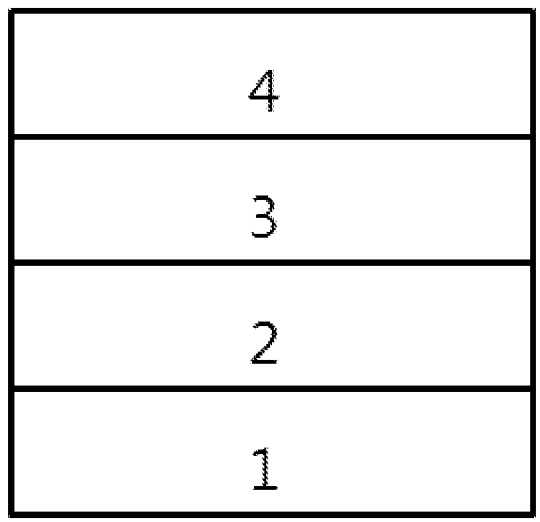
FIG. 1 illustrates an example of an organic light emitting device composed of a substrate 1, a positive electrode 2, a light emitting layer 3, and a negative electrode 4.

Hereinafter, the present specification will be described in more detail.

An exemplary embodiment of the present specification provides the compound represented by Formula 1.

Examples of the substituents will be described below, but are not limited thereto.

In the present specification, the term "substituted or unsubstituted" means that a group is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group; an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group, or a substituent to which two or more substituents among the substituents exemplified above are linked is substituted or unsubstituted. For example, "the substituent to which two or more substituents are linked" may be a biphenyl group. That is, the biphenyl group may also be an aryl group, and may be interpreted as a substituent to which two phenyl groups are linked.

According to an exemplary embodiment of the present specification, the term "substituted or unsubstituted" may preferably mean that a group is unsubstituted or substituted with one or more substituents selected from the group consisting of deuterium, an alkyl group, an alkoxy group, and an aryl group.

According to an exemplary embodiment of the present specification, the compound represented by Formula 1 may be unsubstituted or substituted with at least one deuterium.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the number of carbon atoms of the carbonyl group is not particularly limited, but is preferably 1 to 40. Specifically, the carbonyl group may be a compound having the following structure, but is not limited thereto:

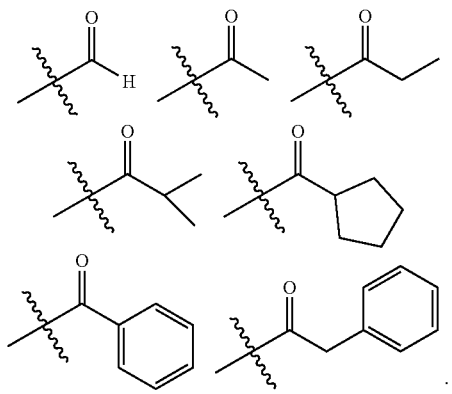

In the present specification, in the ester group, the oxygen of the ester group may be substituted with a straight-chained, branched, or cyclic alkyl group having 1 to 25 carbon atoms, or an aryl group having 6 to 25 carbon atoms. Specifically, the ester group may be a compound having the following structure, but is not limited thereto:

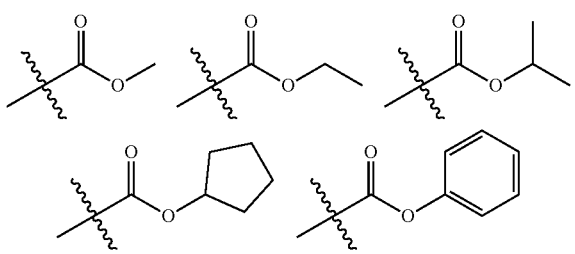

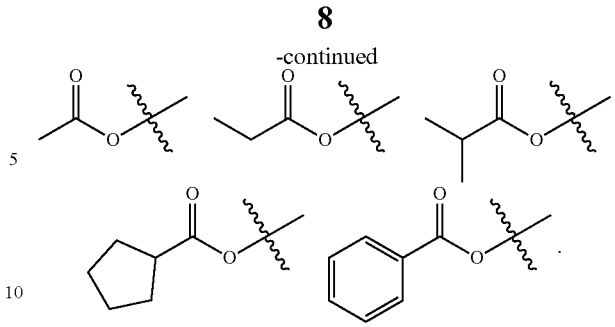

In the present specification, the number of carbon atoms of the imide group is not particularly limited, but is preferably 1 to 25. Specifically, the imide group may be a compound having the following structure, but is not limited thereto:

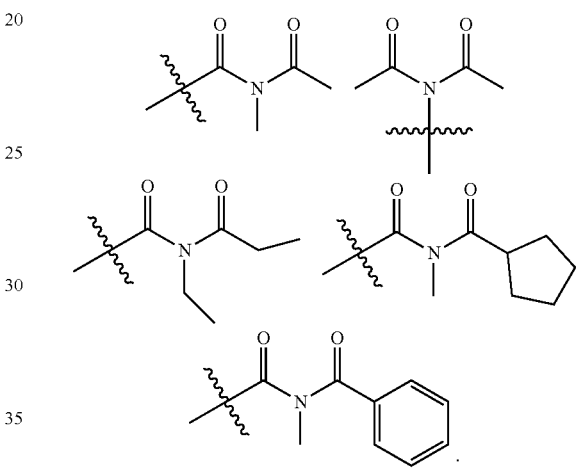

In the present specification, the silyl group may be represented by a formula of —SiRR'R", and R, R', and R" may be each hydrogen; a substituted or unsubstituted alkyl group; or a substituted or unsubstituted aryl group. Specific examples of the silyl group include a trimethyl-silyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, the boron group may be represented by a formula of —BRR'R", and R, R', and R" may be each hydrogen; a substituted or unsubstituted alkyl group; or a substituted or unsubstituted aryl group. Specific examples of the boron group include a trimethylboron group, a triethylboron group, a t-butyl-dimethylboron group, a triphenylboron group, a phenylboron group, and the like, but are not limited thereto.

In the present specification, examples of the halogen group include fluorine, chlorine, bromine or iodine.

In the present specification, the alkyl group may be straight-chained or branched, and the number of carbon atoms thereof is not particularly limited, but is preferably 1 to 40. According to an exemplary embodiment, the number of carbon atoms of the alkyl group is 1 to 20. According to another exemplary embodiment, the number of carbon atoms of the alkyl group is 1 to 10. According to still another exemplary embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentyl-methyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 4-methylhexyl, 5-methylhexyl, and the like, but are not limited thereto.

In the present specification, the alkenyl group may be straight-chained or branched, and the number of carbon atoms thereof is not particularly limited, but is preferably 2 to 40. According to an exemplary embodiment, the number of carbon atoms of the alkenyl group is 2 to 20. According to another exemplary embodiment, the number of carbon atoms of the alkenyl group is 2 to 10. According to still another exemplary embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, the cycloalkyl group is not particularly limited, but has preferably 3 to 60 carbon atoms, and according to an exemplary embodiment, the number of carbon atoms of the cycloalkyl group is 3 to 30. According to yet another exemplary embodiment, the number of carbon atoms of the cycloalkyl group is 3 to 20. According to still yet another exemplary embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including the two or more aryl groups may include a monocyclic aryl group, a polycyclic aryl group, or both a monocyclic aryl group and a polycyclic aryl group.

Specific examples of the arylamine group include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group, and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroaryl group in the heteroarylamine group may be a monocyclic hetero-cyclic group or a polycyclic hetero-cyclic group. The heteroarylamine group including the two or more hetero-cyclic groups may include a monocyclic hetero-cyclic group, a polycyclic hetero-cyclic group, or both a monocyclic hetero-cyclic group and a polycyclic hetero-cyclic group.

In the present specification, the arylheteroarylamine group means an amine group substituted with an aryl group and a hetero-cyclic group.

In the present specification, examples of the arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group or a polycyclic aryl group. The arylphosphine group including the two or more aryl groups may include a monocyclic aryl group, a polycyclic aryl group, or both a monocyclic aryl group and a polycyclic aryl group.

In the present specification, examples of the arylamine group mean a substituted or unsubstituted monocyclic diarylamine group, a substituted or unsubstituted polycyclic diarylamine group, or a substituted or unsubstituted monocyclic and polycyclic diarylamine group.

In the present specification, the aryl group is not particularly limited, but has preferably 6 to 60 carbon atoms, and may be a monocyclic aryl group or a polycyclic aryl group. According to an exemplary embodiment, the number of carbon atoms of the aryl group is 6 to 30. According to an exemplary embodiment, the number of carbon atoms of the aryl group is 6 to 20. When the aryl group is a monocyclic aryl group, examples of the monocyclic aryl group include a phenyl group, a biphenyl group, a terphenyl group, and the like, but are not limited thereto. Examples of the polycyclic aryl group include a naphthyl group, an anthracenyl group, a phenanthryl group, a pyrenyl group, a perylenyl group, a chrysenyl group, a fluorenyl group, a triphenylene group, and the like, but are not limited thereto.

In the present specification, the fluorenyl group may be substituted, and two substituents may combine with each other to form a spiro structure.

When the fluorenyl group is substituted, the fluorenyl group may be

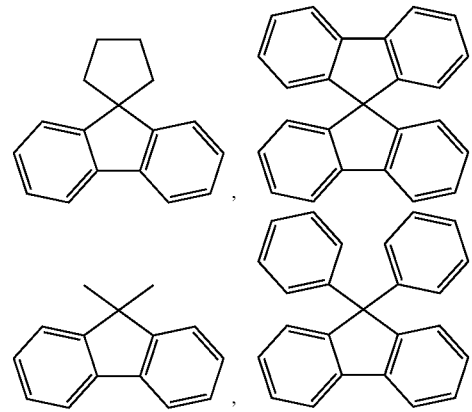

and the like. However, the fluorenyl group is not limited thereto.

In the present specification, the hetero-cyclic group is a hetero-cyclic group including one or more of N, O, P, S, Si, and Se as a hetero atom, and the number of carbon atoms thereof is not particularly limited, but is preferably 2 to 60. Examples of the hetero-cyclic group include a thiophene group, a furan group, a pyrrole group, an imidazole group, a thiazole group, an oxazole group, an oxadiazole group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the description on the above-described hetero-cyclic group may be applied to a heteroaryl group except for an aromatic group.

In the present specification, the description on the above-described aryl group may be applied to an aryl group of an aryloxy group, an arylthioxy group, an arylsulfoxy group, an arylphosphine group, an aralkyl group, an aralkylamine group, an aralkenyl group, an alkylaryl group, an arylamine group, and an arylheteroarylamine group.

In the present specification, the description on the above-described alkyl group may be applied to an alkyl group of an alkylthioxy group, an alkylsulfoxy group, an aralkyl group, an aralkylamine group, an alkylaryl group, and an alkylamine group.

In the present specification, the description on the above-described hetero-cyclic group may be applied to a heteroaryl group of a heteroaryl group, a heteroarylamine group, and an arylheteroarylamine group.

In the present specification, the description on the above-described alkenyl group may be applied to an alkenyl group of an aralkenyl group.

In the present specification, the description on the above-described aryl group may be applied to an arylene except for a divalent arylene group.

In the present specification, the description on the above-described hetero-cyclic group may be applied to a heteroarylene except for a divalent heteroarylene group.

In the present specification, the meaning of combining with an adjacent group to form a ring means of combining with an adjacent group to form a substituted or unsubstituted aliphatic hydrocarbon ring; a substituted or unsubstituted aromatic hydrocarbon ring; a substituted or unsubstituted aliphatic hetero ring; a substituted or unsubstituted aromatic hetero ring; and a condensed ring thereof.

In the present specification, the aliphatic hydrocarbon ring means a ring composed only of carbon and hydrogen atoms as a ring which is not an aromatic group.

In the present specification, examples of the aromatic hydrocarbon ring include a phenyl group, a naphthyl group, an anthracenyl group, and the like, but are not limited thereto.

In the present specification, the aliphatic hetero ring means an aliphatic ring including one or more of hetero atoms.

In the present specification, the aromatic hetero ring means an aromatic ring including one or more of hetero atoms.

In the present specification, the aliphatic hydrocarbon ring, the aromatic hydrocarbon ring, the aliphatic hetero ring, and the aromatic hetero ring may be monocyclic or polycyclic.

According to an exemplary embodiment of the present specification, Formula 1 may be represented by any one of the following Formulae 2 to 4.

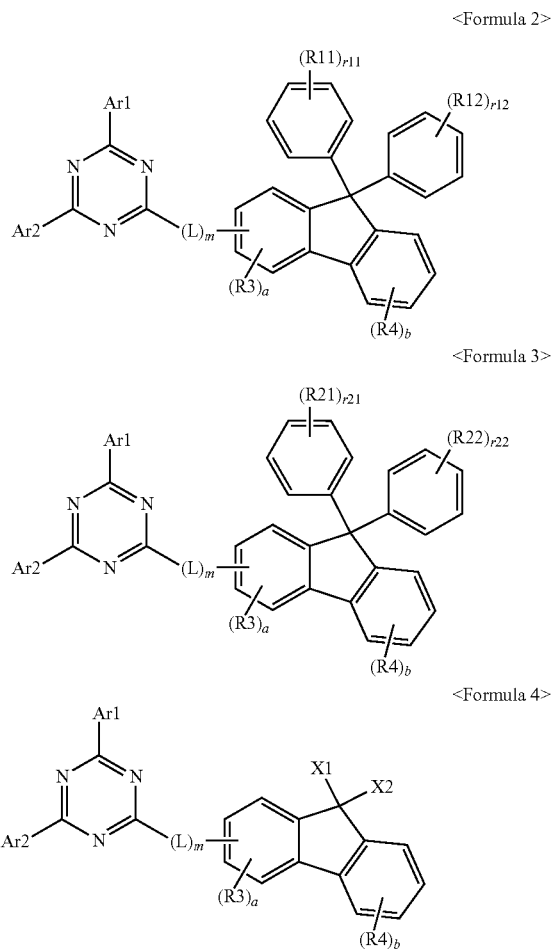

In Formulae 2 to 4, the definition of Ar1, Ar2, L, R3, R4, a, b, and m is the same as defined in Formula 1, the definition of R11, R12, R21, and R22 is the same as the definition of R3 and R4, X1 and X2 are the same as or different from each other, and each independently is hydrogen, deuterium, a halogen group, a nitrile group, a nitro group, a hydroxy group, a carbonyl group, an ester group, an imide group, an amino group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted alkylamine group, a substituted or unsubstituted aralkylamine group, a substituted or unsubstituted heteroarylamine group, a substituted or unsubstituted arylamine group, a substituted or unsubstituted arylheteroarylamine group, a substituted or unsubstituted arylphosphine group, or a substituted or unsubstituted phosphineoxide group, or may combine with an adjacent group to form a substituted or unsubstituted ring;

r11 and r12 are the same as or different from each other, and each independently is an integer of 0 to 5;

r21 and r22 are the same as or different from each other, and each independently is an integer of 0 to 4; and when r11, r12, r21, and r22 are each 2 or more, the structures in the parenthesis are the same as or different from each other.

According to an exemplary embodiment of the present specification, Formula 1 may be represented by any one of the following Formulae 5 to 8:

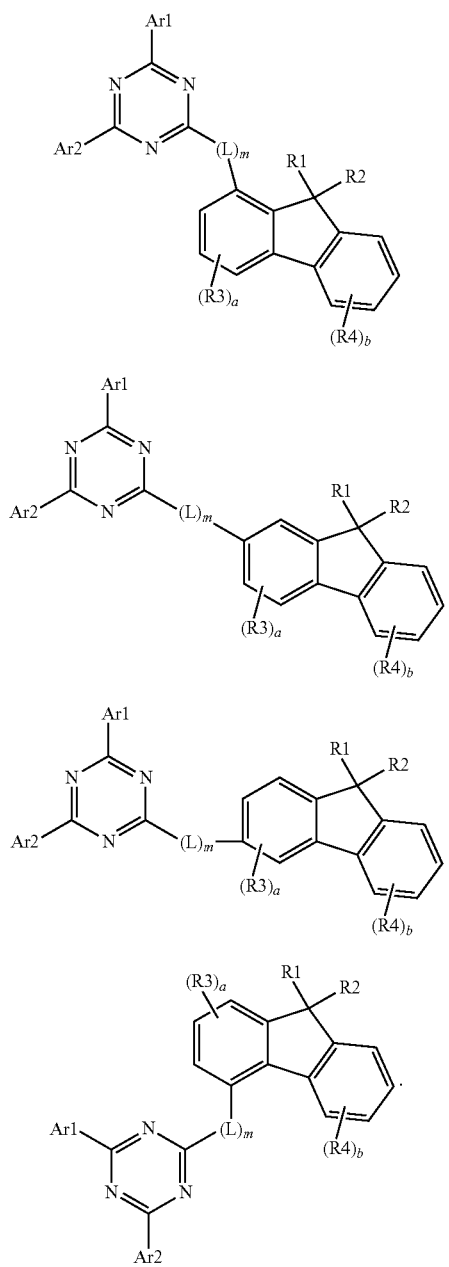

<Formula 5>

<Formula 6>

<Formula 7>

<Formula 8>

In Formulae 5 to 8,
the definition of Ar1, Ar2, L, R1 to R4, m, a, and b is the same as defined in Formula 1.

According to an exemplary embodiment of the present specification, Formula 2 may be represented by any one of the following Formulae 2-1 to 2-4:

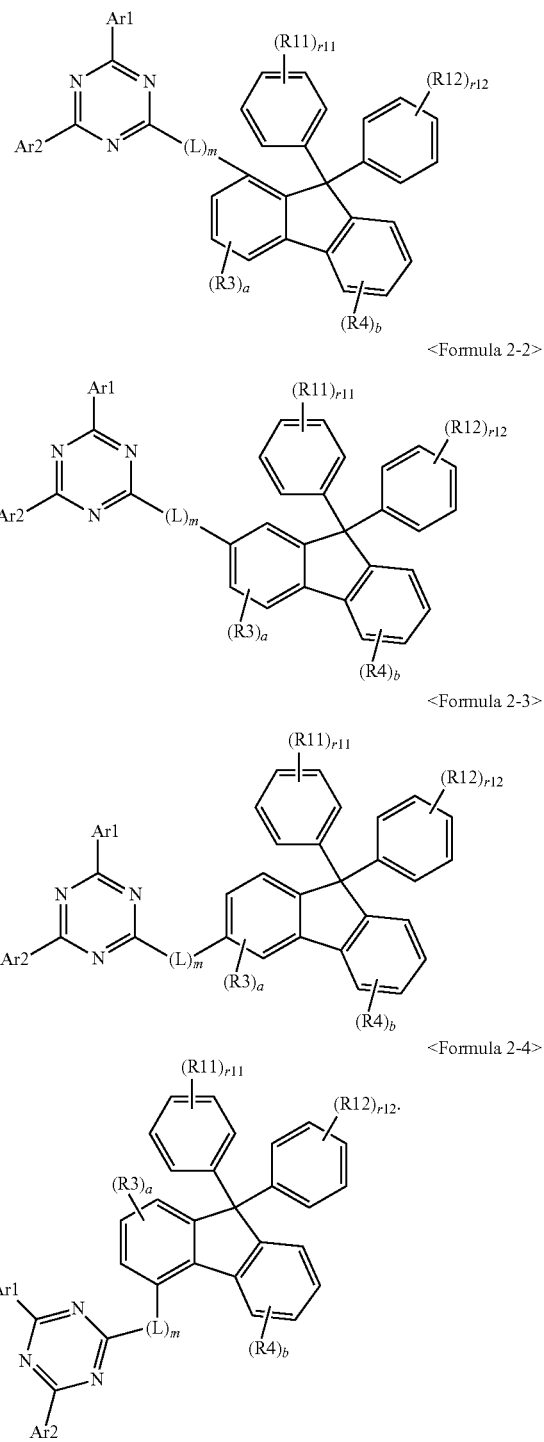

<Formula 2-1>

<Formula 2-2>

<Formula 2-3>

<Formula 2-4>

In Formulae 2-1 to 2-4:
the definition of Ar1, Ar2, L, R3, R4, a, and b is the same as defined in Formula 1; and
the definition of R11, R12, r11, and r12 is the same as defined in Formula 2.

According to an exemplary embodiment of the present specification, Formula 3 may be represented by any one of the following Formulae 3-1 to 3-4:

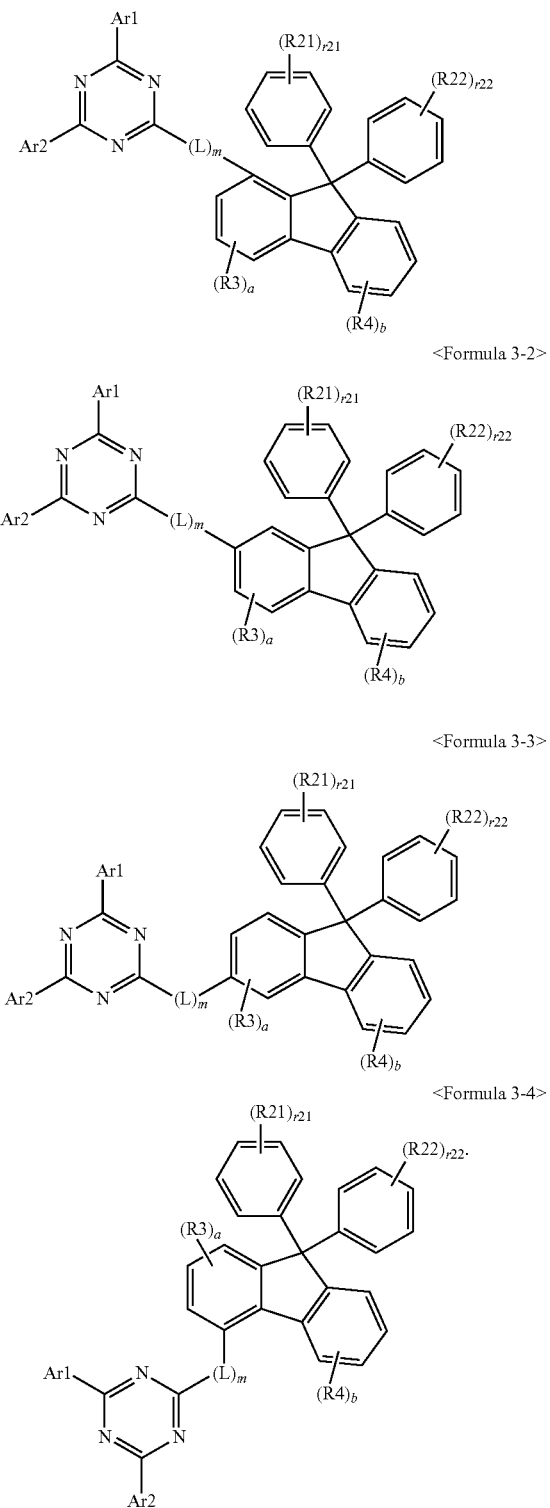

<Formula 3-1>
<Formula 3-2>
<Formula 3-3>
<Formula 3-4>

In Formulae 3-1 to 3-4:

the definition of Ar1, Ar2, L, R3, R4, a, and b is the same as defined in Formula 1; and the definition of R21, R22, r21, and r22 is the same as defined in Formula 3.

According to an exemplary embodiment of the present specification, X1 and X2 are the same as or different from each other, and each independently a substituted or unsubstituted alkyl group.

According to an exemplary embodiment of the present specification, X1 and X2 are the same as or different from each other, and each independently an alkyl group.

According to an exemplary embodiment of the present specification, X1 and X2 are a methyl group.

According to an exemplary embodiment of the present specification, Ar1 and Ar2 are the same as each other, and each is:

a phenyl group, which is unsubstituted or substituted with one or more substituents selected from the group consisting of deuterium and an alkyl group;

a biphenyl group, which is unsubstituted or substituted with one or more substituents selected from the group consisting of deuterium, an alkyl group, and an aryl group;

a naphthyl group, which is unsubstituted or substituted with one or more substituents selected from the group consisting of deuterium, an alkyl group, and an aryl group; or a phenanthryl group, which is unsubstituted or substituted with one or more substituents selected from the group consisting of deuterium, an alkyl group, and an aryl group.

According to an exemplary embodiment of the present specification, Ar1 and Ar2 are the same as each other, and each is a phenyl group, which is unsubstituted or substituted with deuterium; a biphenyl group, which is unsubstituted or substituted with deuterium; a naphthyl group, which is unsubstituted or substituted with deuterium; or a phenanthryl group, which is unsubstituted or substituted with deuterium.

According to an exemplary embodiment of the present specification, Ar1 and Ar2 are the same as each other, and each is a phenyl group; a biphenyl group; a naphthyl group; or a phenanthryl group.

According to an exemplary embodiment of the present specification, R1 and R2 are the same as or different from each other, and each independently is hydrogen; deuterium; a halogen group; a nitrile group; a nitro group; a hydroxy group; a carbonyl group; an ester group; an imide group; an amino group; a silyl group; a boron group; an alkyl group; a cycloalkyl group; an alkoxy group; an aryloxy group; an alkylthioxy group; an arylthioxy group; an alkylsulfoxy group; an arylsulfoxy group; an alkenyl group; an aralkyl group; an aralkenyl group; an alkylaryl group; an alkylamine group; an aralkylamine group; a heteroarylamine group; an arylamine group; an arylheteroarylamine group; an arylphosphine group; a phosphine oxide group; an aryl group, which is unsubstituted or substituted with deuterium, an alkyl group, or an alkoxy group; or a hetero-cyclic group, or may combine with an adjacent group to form a ring.

According to an exemplary embodiment of the present specification, R1 and R2 are the same as or different from each other, and each independently is hydrogen, deuterium, a substituted or unsubstituted alkyl group, or a substituted or unsubstituted aryl group, or combine with each other to form a substituted or unsubstituted ring.

According to an exemplary embodiment of the present specification, R1 and R2 are the same as or different from each other, and each independently is hydrogen; deuterium; an alkyl group, which is unsubstituted or substituted with one or more substituents selected from the group consisting of deuterium, a halogen group, a nitrile group, a nitro group, a hydroxy group, a carbonyl group, an ester group, an imide group, an amino group, a phosphineoxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; or an aryl group, which is unsubstituted or substituted with one or more substituents selected from the group consisting of deuterium, a halogen group, a nitrile group, a nitro group, a hydroxy group, a carbonyl group, an ester group, an imide group, an amino group, a phosphineoxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group, or combine with each other to form a ring, which is unsubstituted or substituted with one or more substituents selected from the group consisting of deuterium, a halogen group, a nitrile group, a nitro group, a hydroxy group, a carbonyl group, an ester group, an imide group, an amino group, a phosphineoxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group.

According to an exemplary embodiment of the present specification, R1 and R2 are the same as or different from each other, and each independently is hydrogen; deuterium; an alkyl group, which is unsubstituted or substituted with one or more substituents selected from the group consisting of deuterium, an alkyl group, an alkoxy group, and an aryl group; or an aryl group, which is unsubstituted or substituted with one or more substituents selected from the group consisting of deuterium, an alkyl group, an alkoxy group, and an aryl group, or combine with each other to form a ring, which is unsubstituted or substituted with one or more substituents selected from the group consisting of deuterium, an alkyl group, an alkoxy group, and an aryl group.

According to an exemplary embodiment of the present specification, R1 and R2 are the same as or different from each other, and each independently is hydrogen; an alkyl group; or an aryl group, which is unsubstituted or substituted with one or more substituents selected from the group consisting of deuterium, a halogen group, an alkyl group, and an alkoxy group, or combine with each other to form a ring.

According to an exemplary embodiment of the present specification, R1 and R2 are the same as or different from each other, and each independently is a substituted or unsubstituted alkyl group, or a substituted or unsubstituted monocyclic to tricyclic aryl group, or combine with each other to form a substituted or unsubstituted ring.

According to an exemplary embodiment of the present specification, R1 and R2 are the same as or different from each other, and each independently is a substituted or unsubstituted alkyl group, or a substituted or unsubstituted phenyl group, or combine with each other to form a substituted or unsubstituted ring.

According to an exemplary embodiment of the present specification, R1 and R2 are the same as or different from each other, and each independently is hydrogen, deuterium, a halogen group, an alkyl group, and an aryl group, or combine with each other to form a ring.

According to an exemplary embodiment of the present specification, R1 and R2 are the same as or different from each other, and each independently is an alkyl group; and an aryl group, or combine with each other to form a ring.

According to an exemplary embodiment of the present specification, R1 and R2 are the same as or different from each other, and each independently is an alkyl group, or a phenyl group, or combine with each other to form a ring.

According to an exemplary embodiment of the present specification, R1 and R2 are the same as or different from each other, and each independently is a methyl group, or a phenyl group, or combine with each other to form a ring.

According to an exemplary embodiment of the present specification, R3 and R4 are the same as or different from each other, and each independently is hydrogen, deuterium, a halogen group, a nitrile group, a nitro group, a hydroxy group, a carbonyl group, an ester group, an imide group, an amino group, a silyl group, a boron group, an alkyl group, a cycloalkyl group, an alkoxy group, an aryloxy group, an alkylthioxy group, an arylthioxy group, an alkylsulfoxy group, an arylsulfoxy group, an alkenyl group, an aralkyl group, an aralkenyl group, an alkylaryl group, an alkylamine group, an aralkylamine group, an arylphosphine group, or a phosphine oxide group.

According to an exemplary embodiment of the present specification, R3 and R4 are the same as or different from each other, and each independently is hydrogen, deuterium, a halogen group, or an alkyl group.

According to an exemplary embodiment of the present specification, R3 and R4 are hydrogen.

According to an exemplary embodiment of the present specification, R4 is hydrogen.

According to an exemplary embodiment of the present specification, R3 is hydrogen.

According to an exemplary embodiment of the present specification, L is a phenylene, which is unsubstituted or substituted with one or more substituents selected from the group consisting of deuterium, a halogen group, a nitrile group, a nitro group, a hydroxy group, a carbonyl group, an ester group, an imide group, an amino group, a phosphineoxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; or a biphenylylene, which is unsubstituted or substituted with one or more substituents selected from the group consisting of deuterium, a halogen group, a nitrile group, a nitro group, a hydroxy group, a carbonyl group, an ester group, an imide group, an amino group, a phosphineoxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group.

According to an exemplary embodiment of the present specification, L is a direct bond, substituted or unsubstituted arylene, or substituted or unsubstituted heteroarylene.

According to an exemplary embodiment of the present specification, L is phenylene or biphenylylene.

According to an exemplary embodiment of the present specification, L may be any one selected from the following structures:

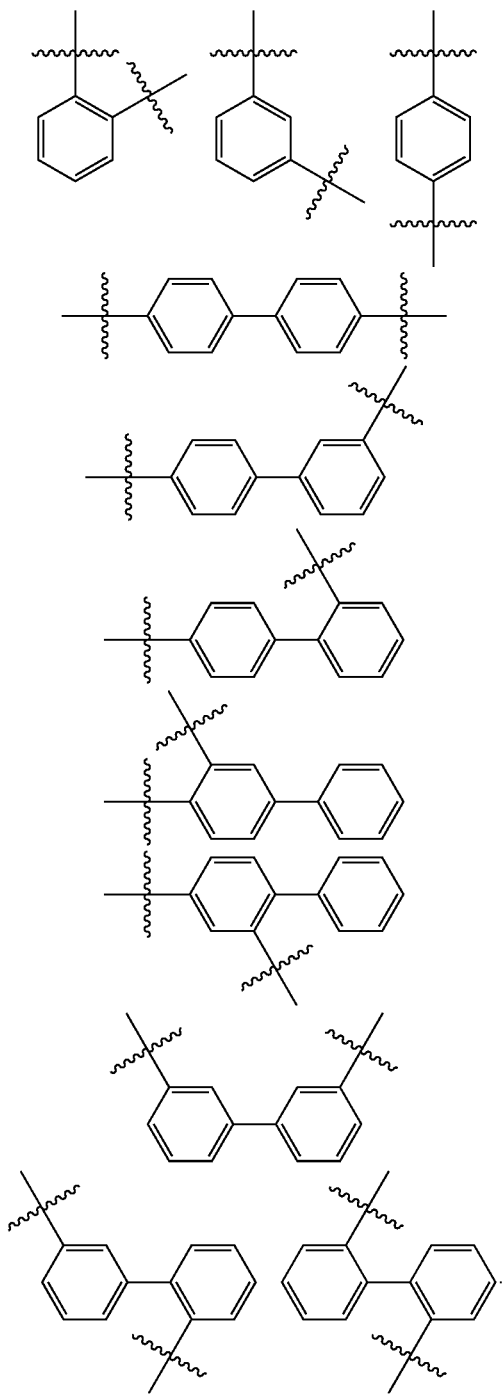

The structures may be unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group, an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a hetero-cyclic group.

According to an exemplary embodiment of the present specification, the

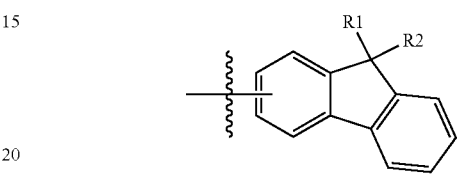

moiety may be any one selected from the following structures:

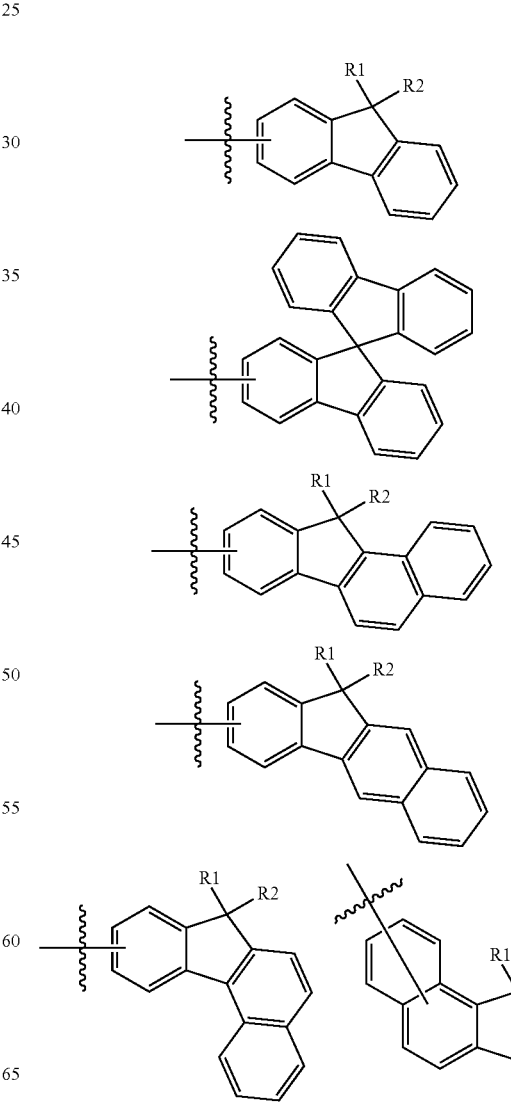

-continued

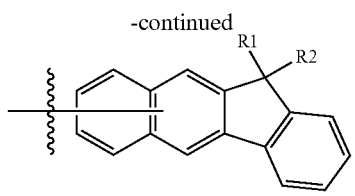

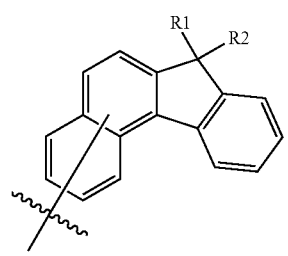

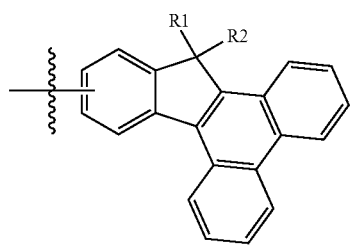

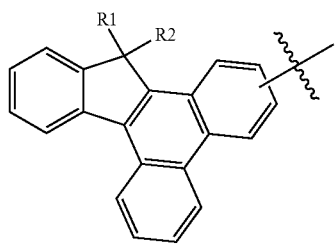

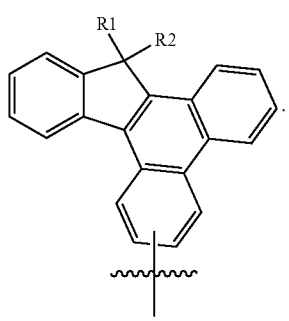

In the structures, the definition of R1 and R2 is the same as defined in Formula 1, and the structures may be unsubstituted or substituted with one or more substituents selected from the group consisting of deuterium; a halogen group; a nitrile group; a nitro group; a hydroxy group; a carbonyl group; an ester group; an imide group; an amino group; a phosphineoxide group, an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a hetero-cyclic group.

According to an exemplary embodiment of the present specification, m is 1.

According to an exemplary embodiment of the present specification, m is 1 or 2.

According to an exemplary embodiment of the present specification, the compound of Formula 1 may be any one selected from the following compounds:

[Compound 1]

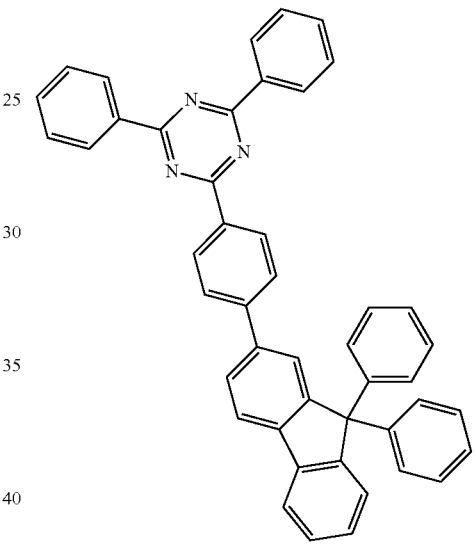

[Compound 2]

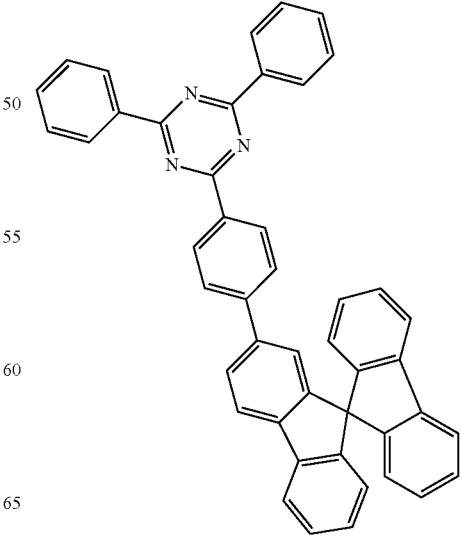

[Compound 3]
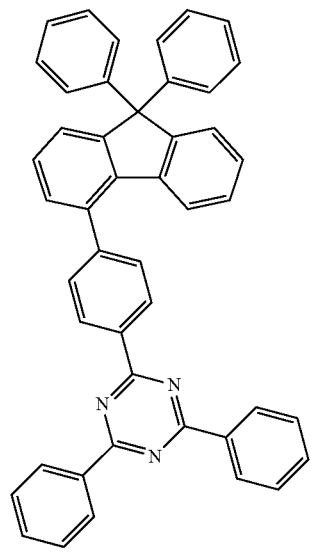
[Compound 4]
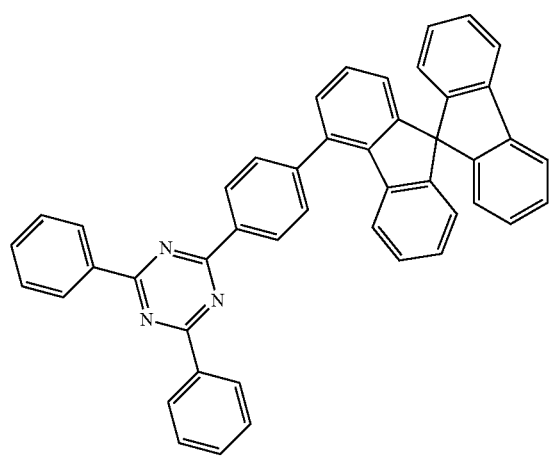
[Compound 5]
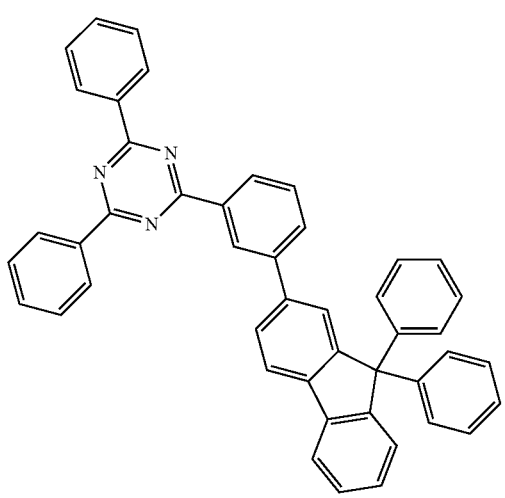
[Compound 6]
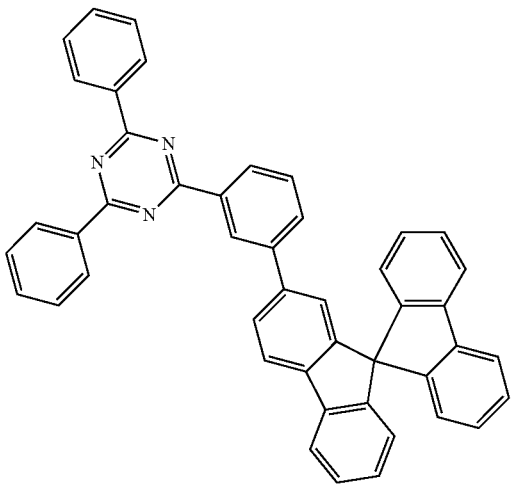
[Compound 7]
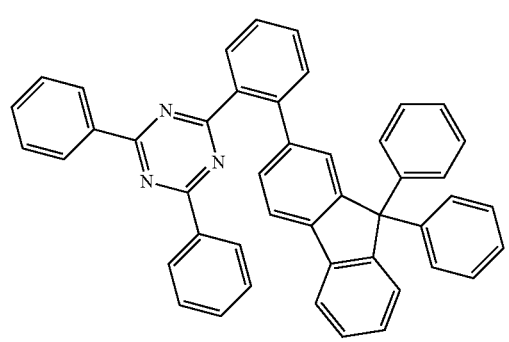
[Compound 8]
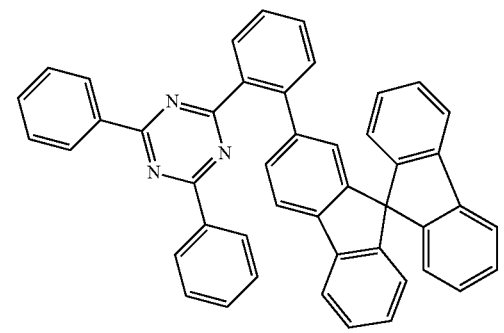

[Compound 9]
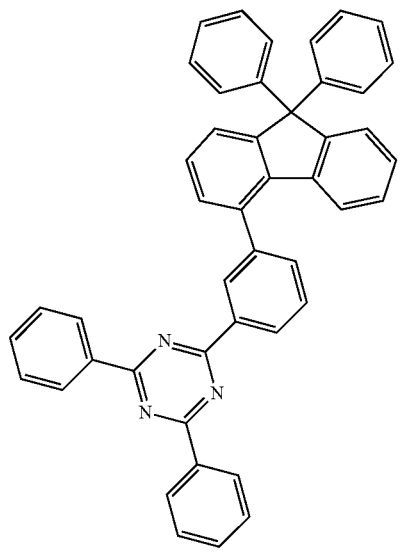
[Compound 12]
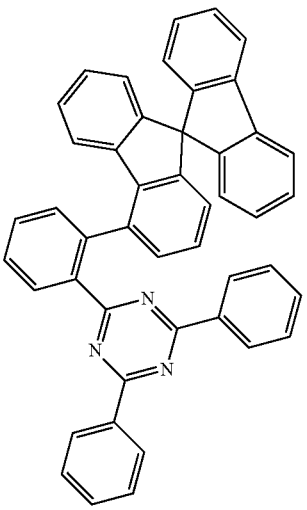
[Compound 10]
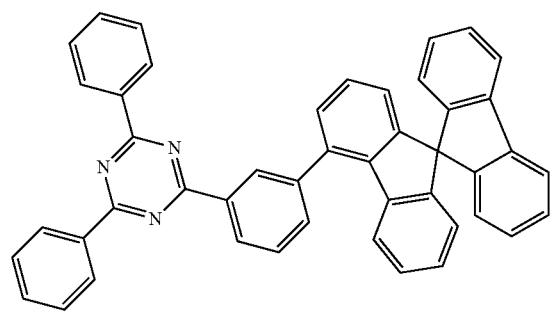
[Compound 11]
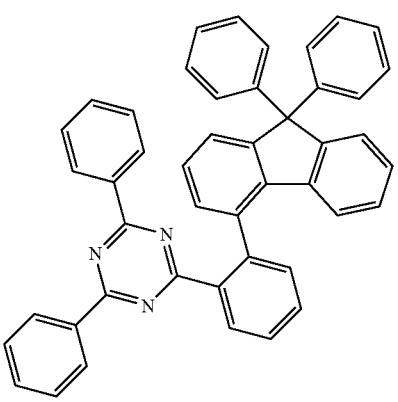
[Compound 13]
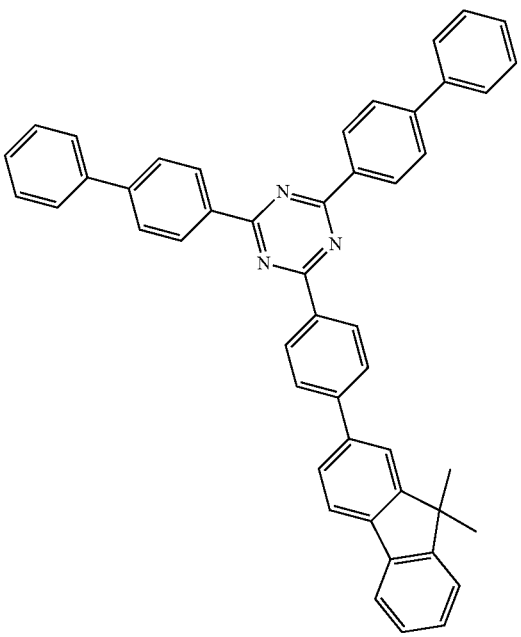

[Compound 14]
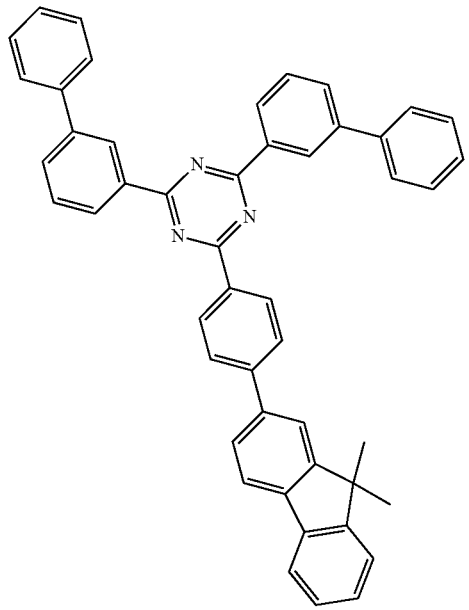
[Compound 15]
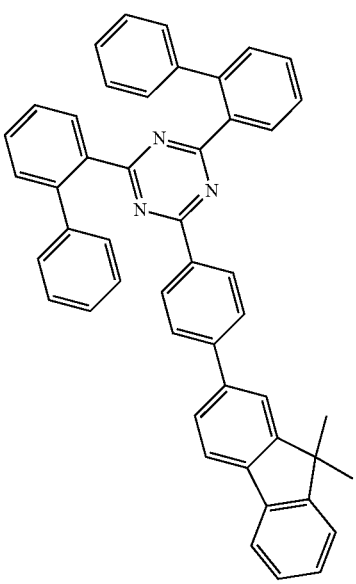
[Compound 16]
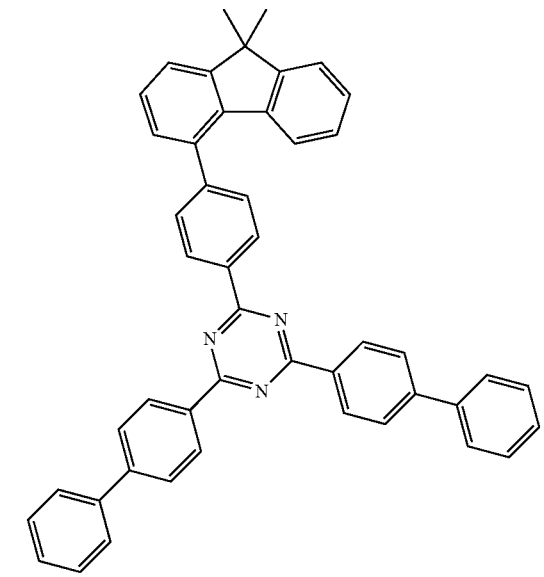
[Compound 17]
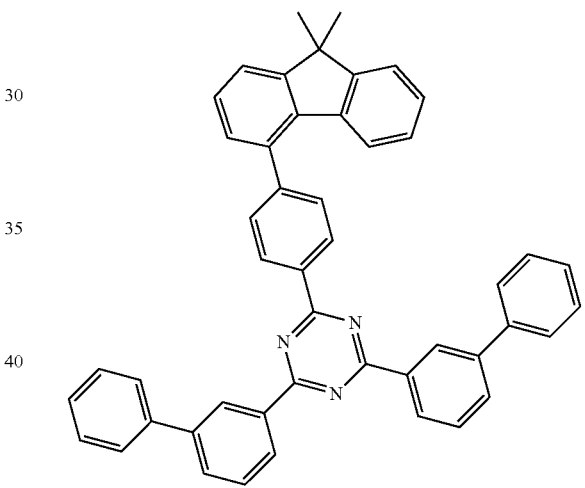
[Compound 18]

[Compound 19]
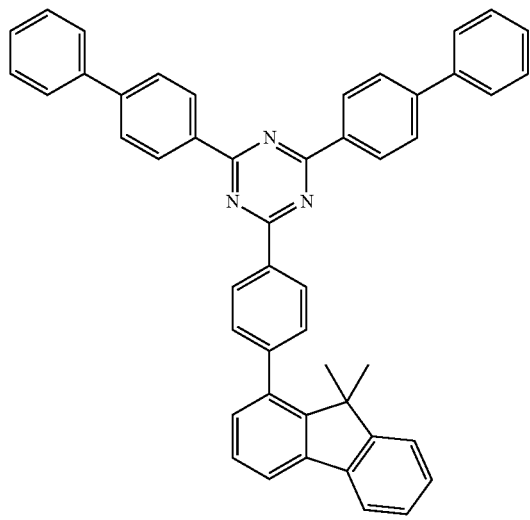
[Compound 20]
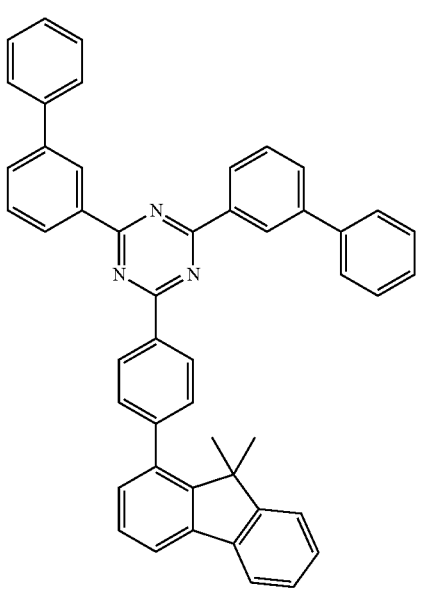
[Compound 21]
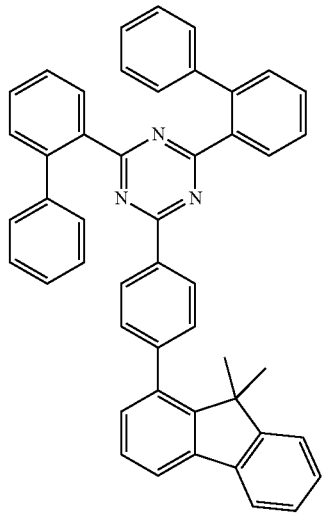
[Compound 22]
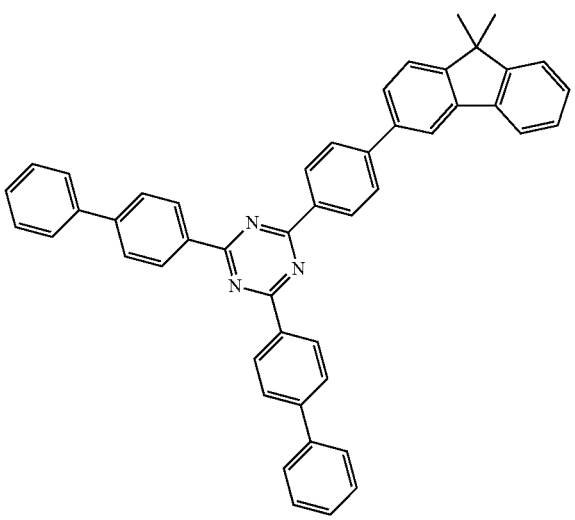
[Compound 23]
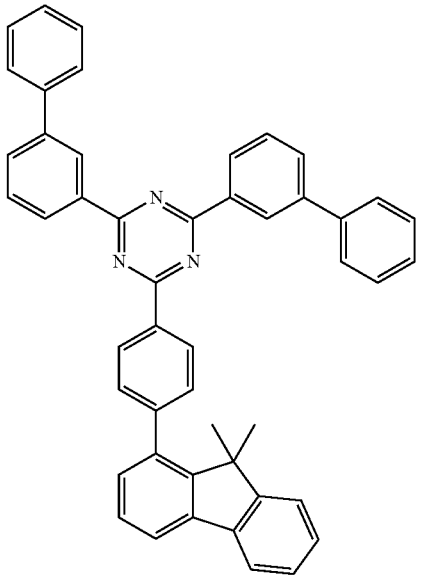
[Compound 24]

[Compound 25]
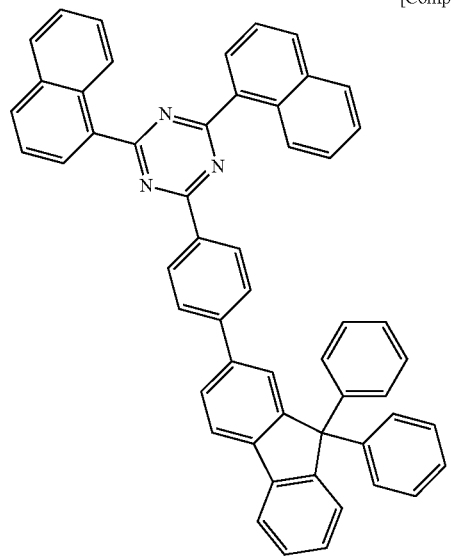
[Compound 27]
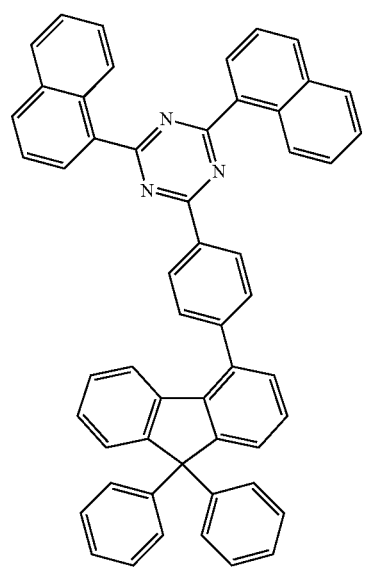
[Compound 26]
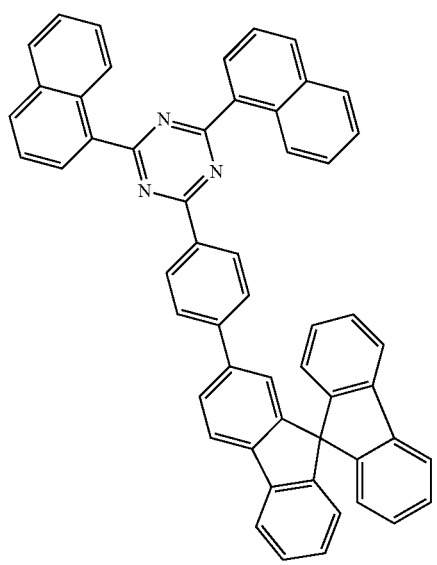
[Compound 28]
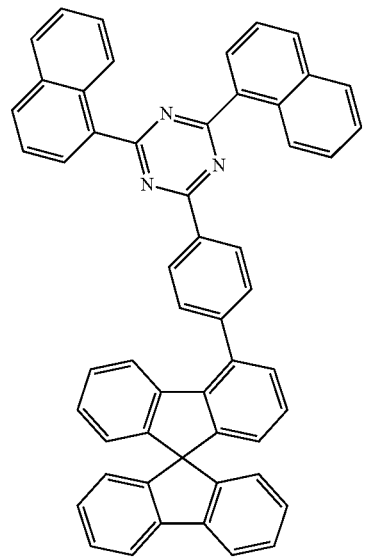

[Compound 29]
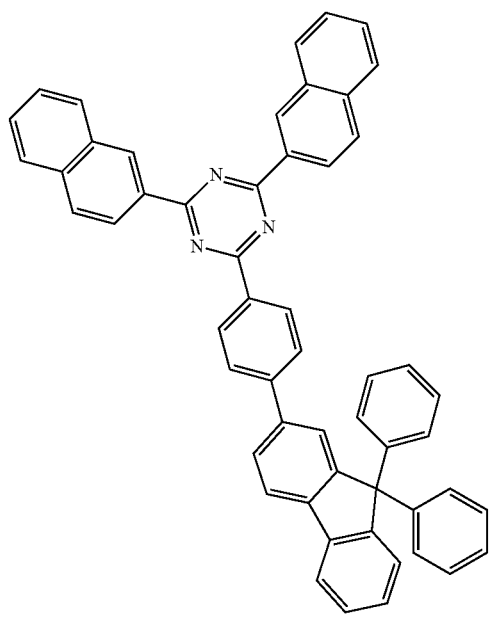
[Compound 31]
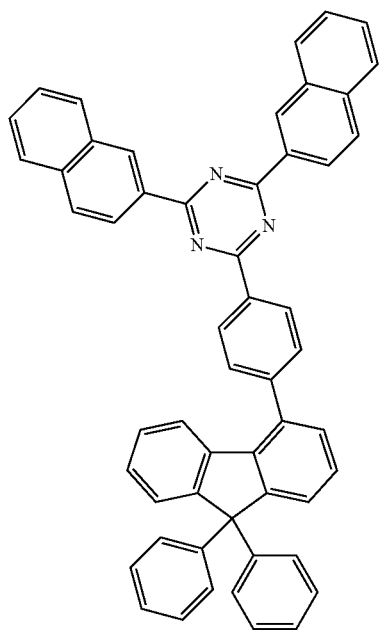
[Compound 30]
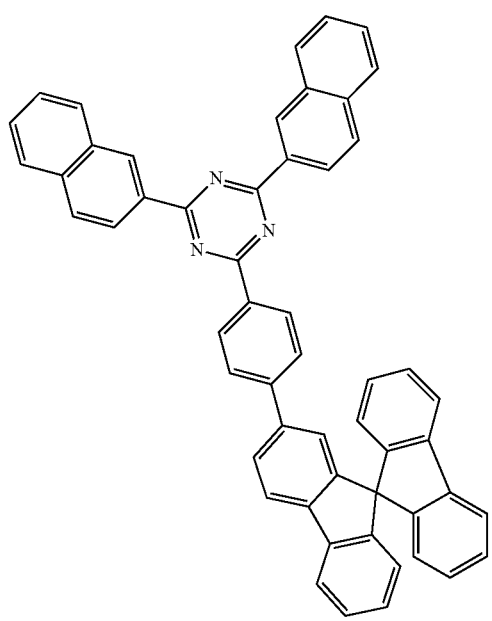
[Compound 32]
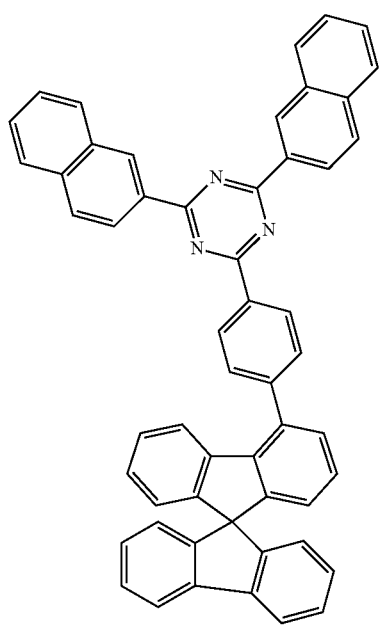

[Compound 33]
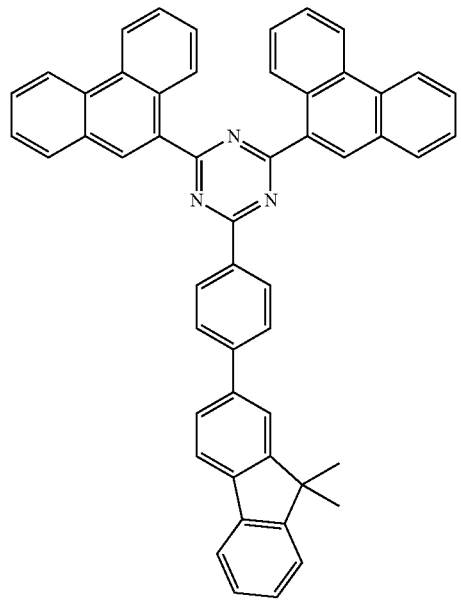
[Compound 34]
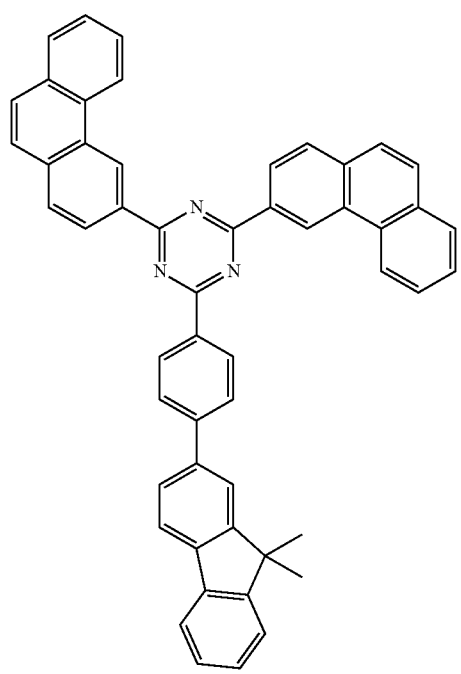
[Compound 35]
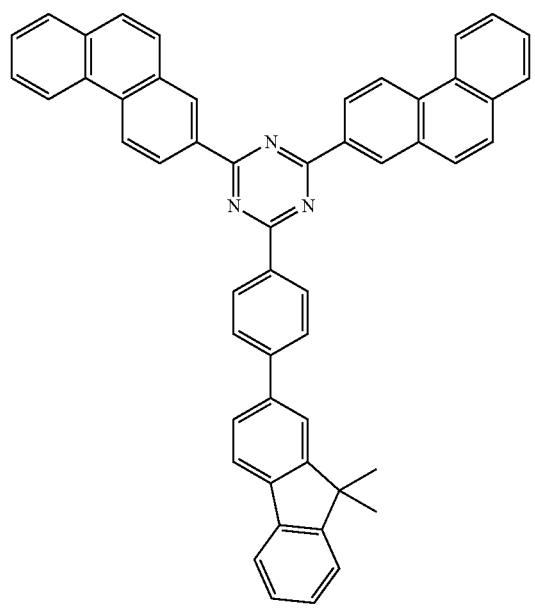
[Compound 36]
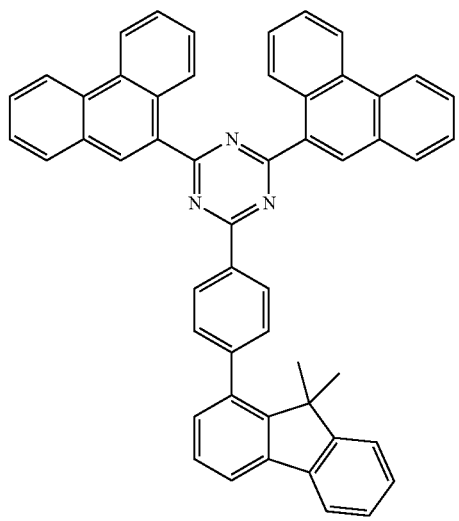

[Compound 37]
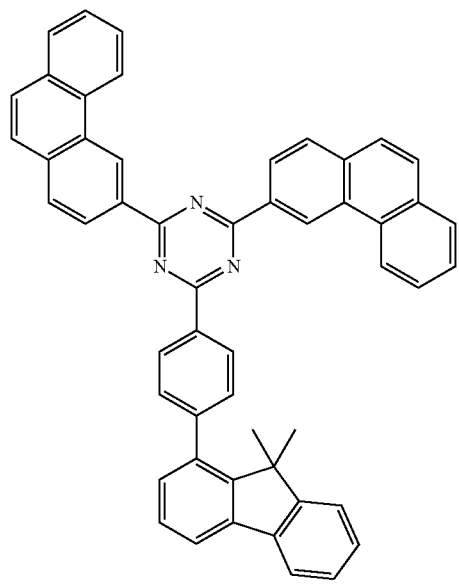
[Compound 38]
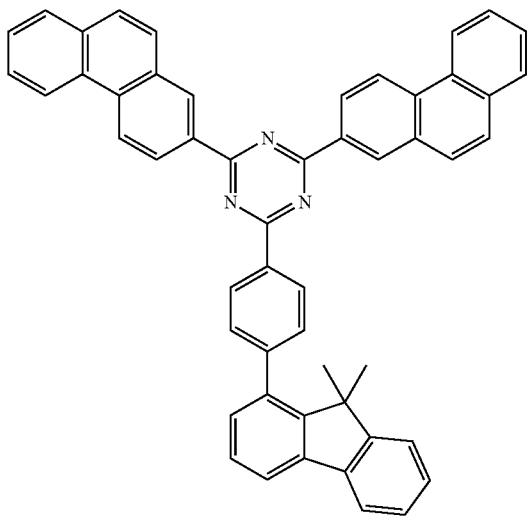
[Compound 39]
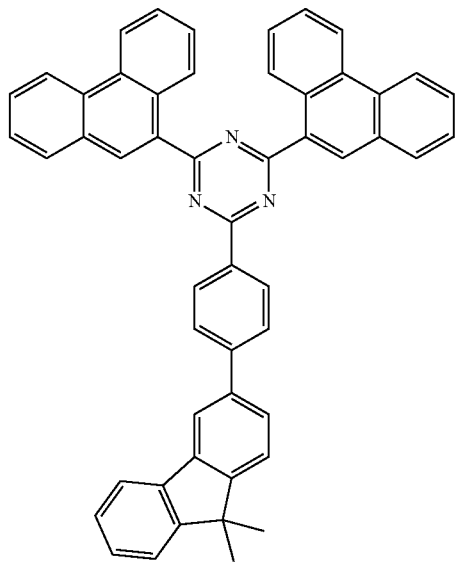
[Compound 40]
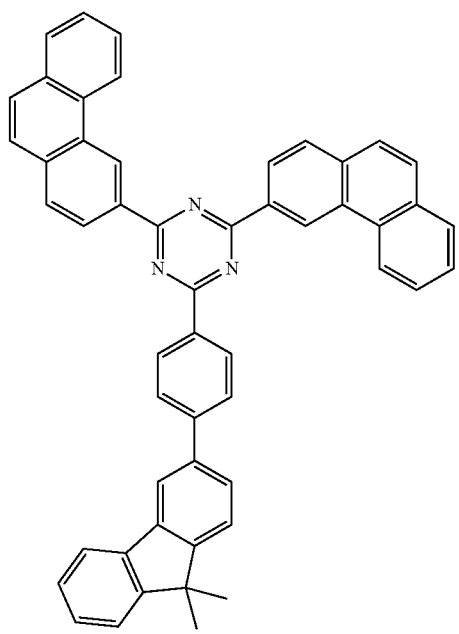

[Compound 41]
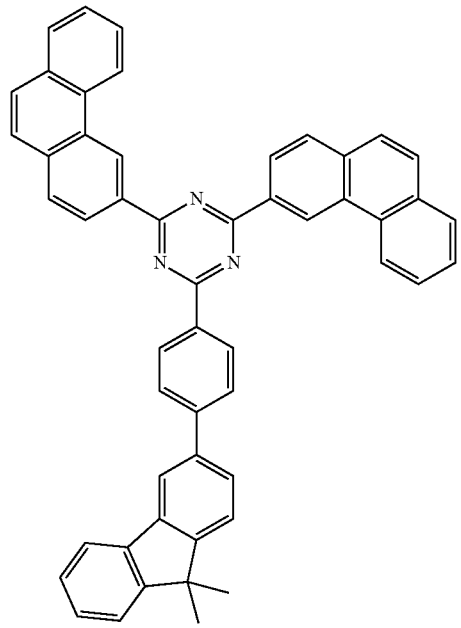
[Compound 42]
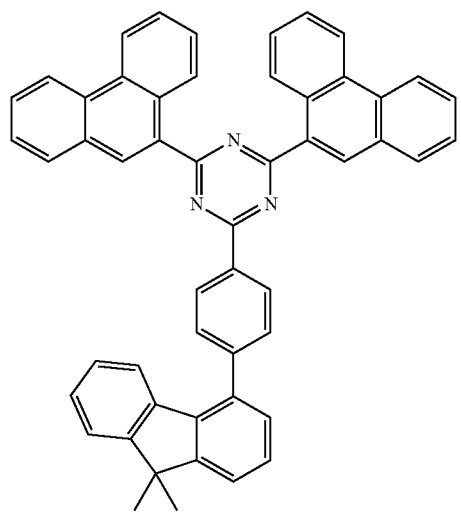
[Compound 43]
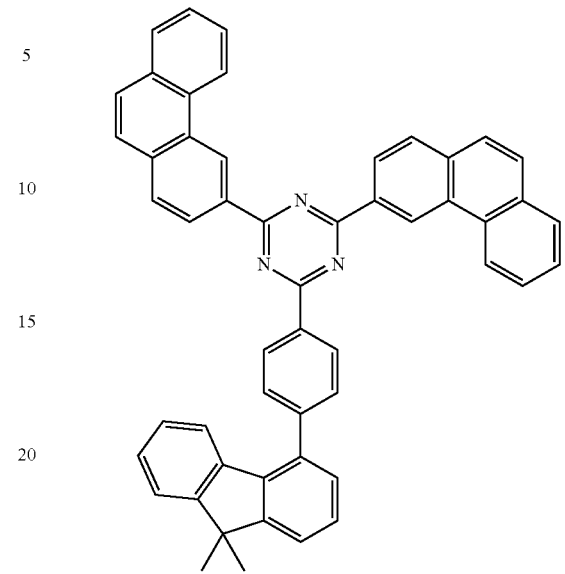
[Compound 44]
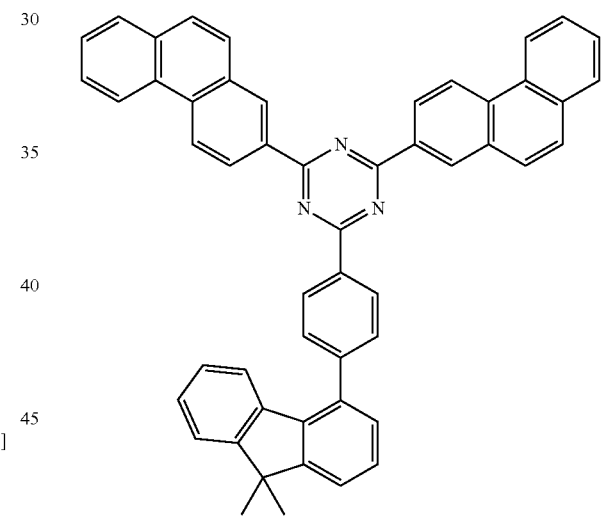
[Compound 45]
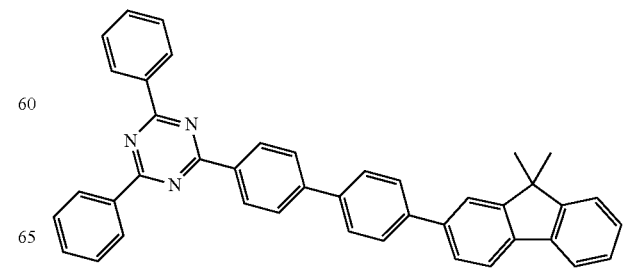

[Compound 46]
[Compound 47]
[Compound 48]
[Compound 49]
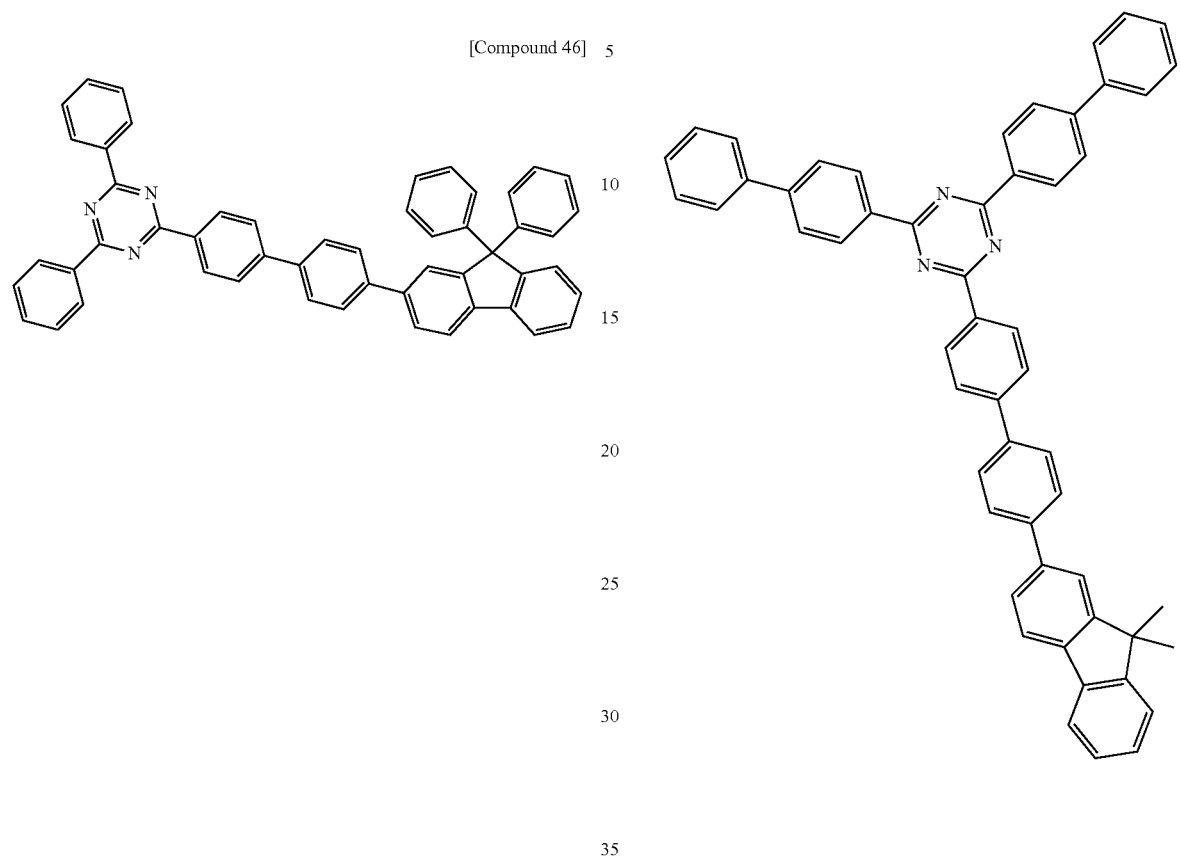
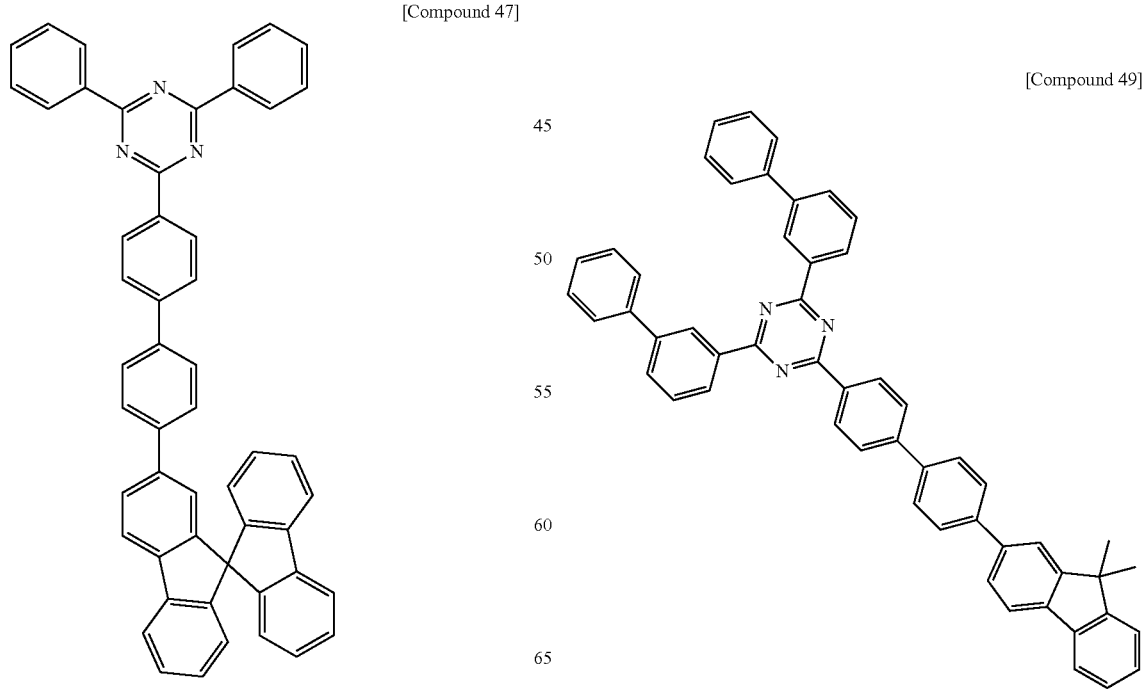

[Compound 50]
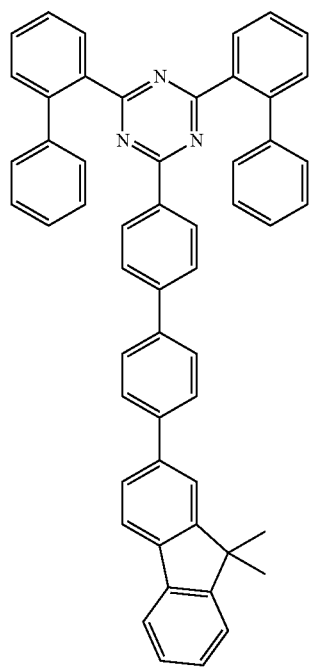
[Compound 52]
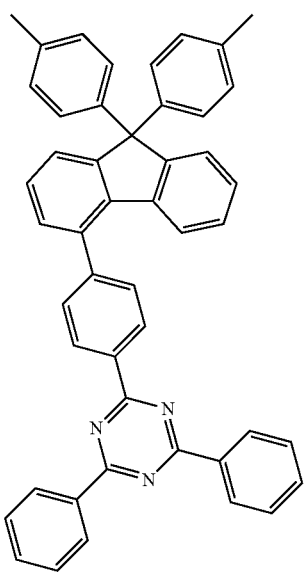
[Compound 51]
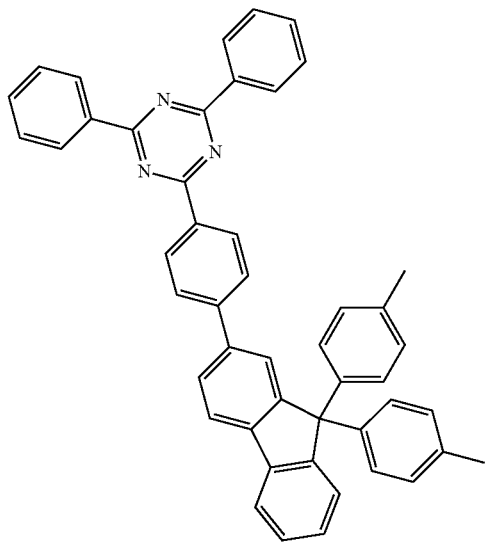
[Compound 53]
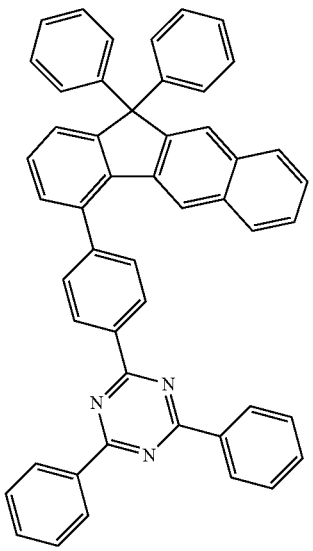

[Compound 54]
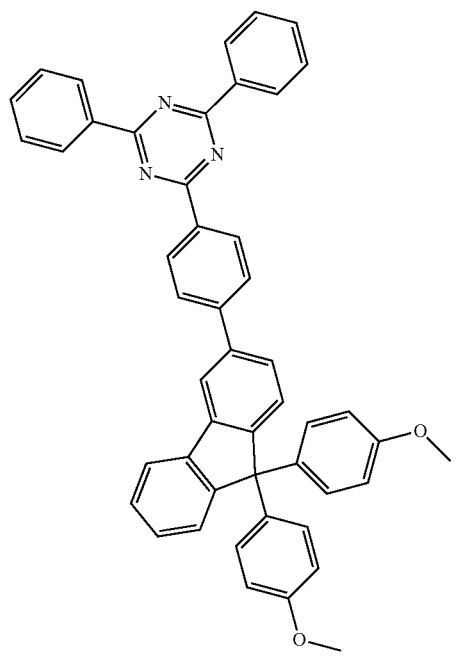
[Compound 56]
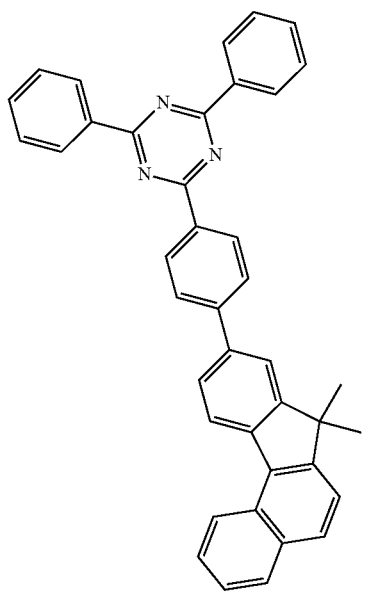
[Compound 55]
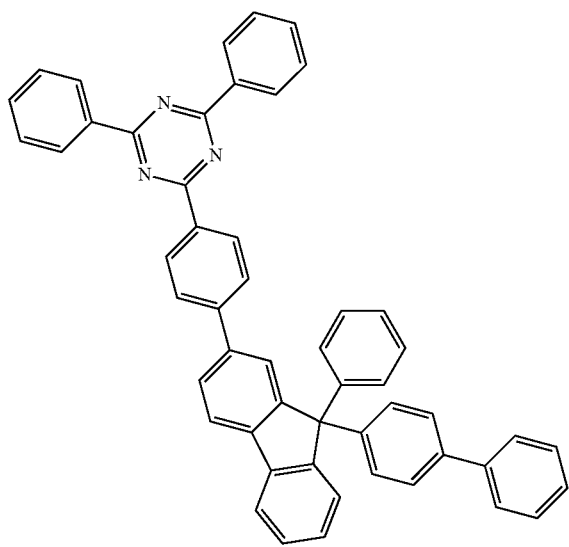
[Compound 57]
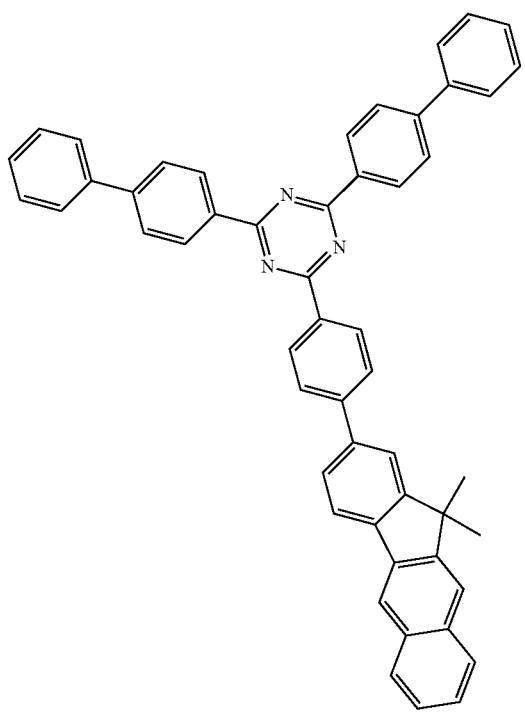

[Compound 58]
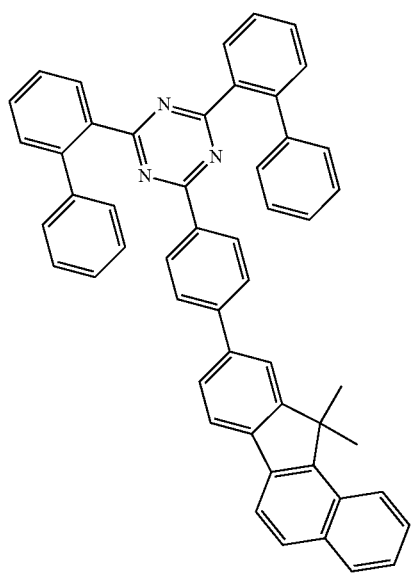
[Compound 60]
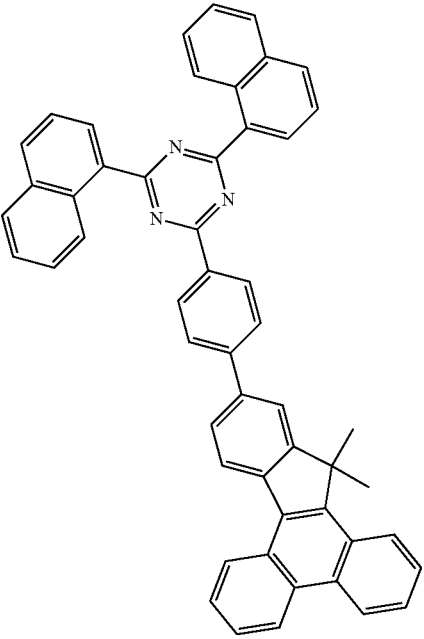
[Compound 59]
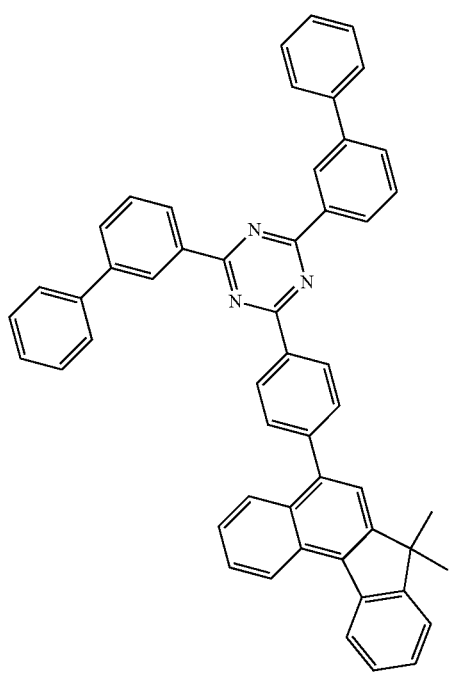
[Compound 61]
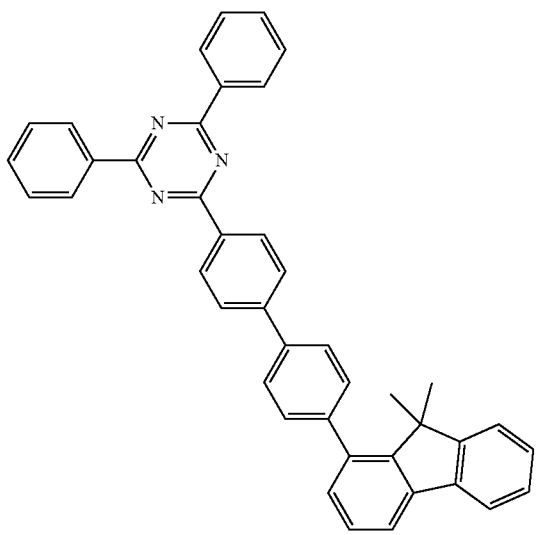

[Compound 62]
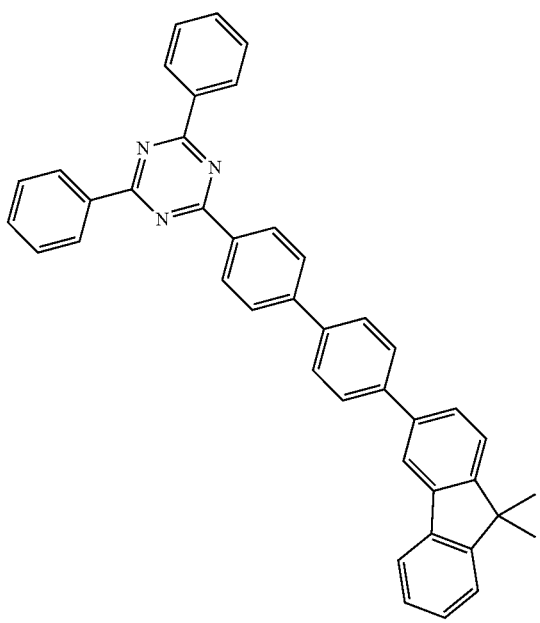
[Compound 64]
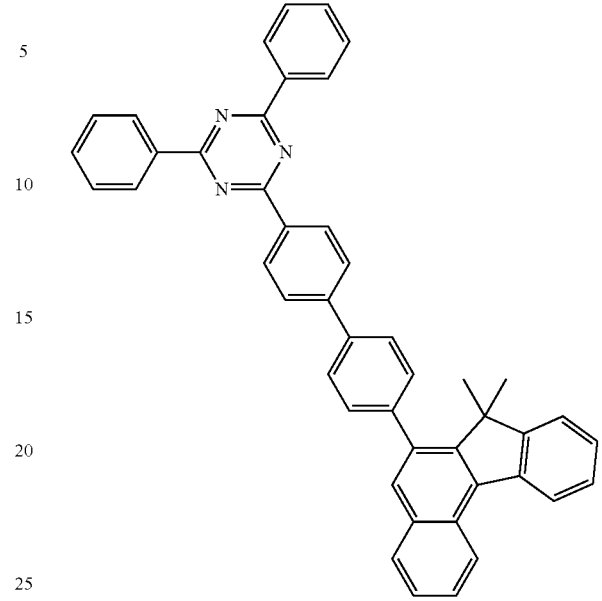
[Compound 63]
[Compound 65]
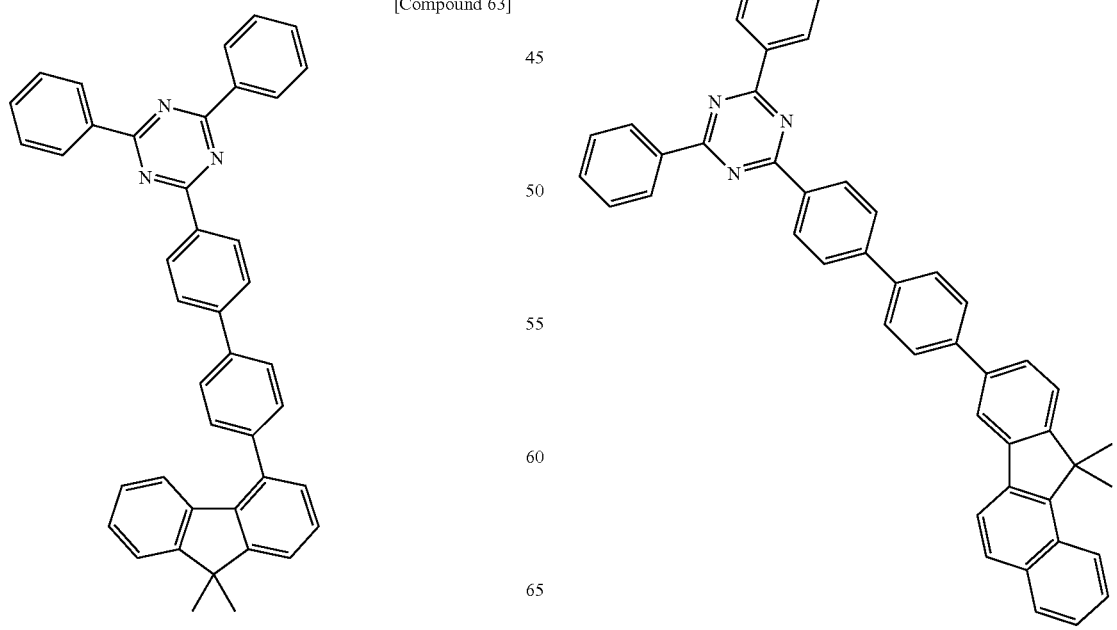

[Compound 66]
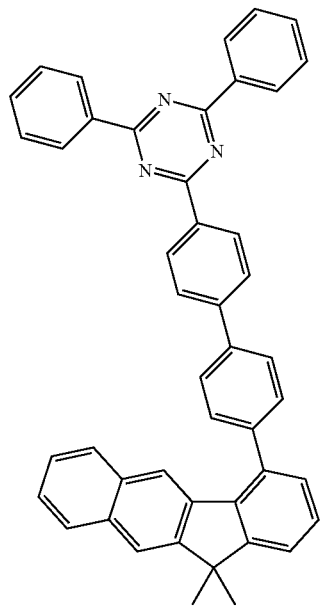
[Compound 67]
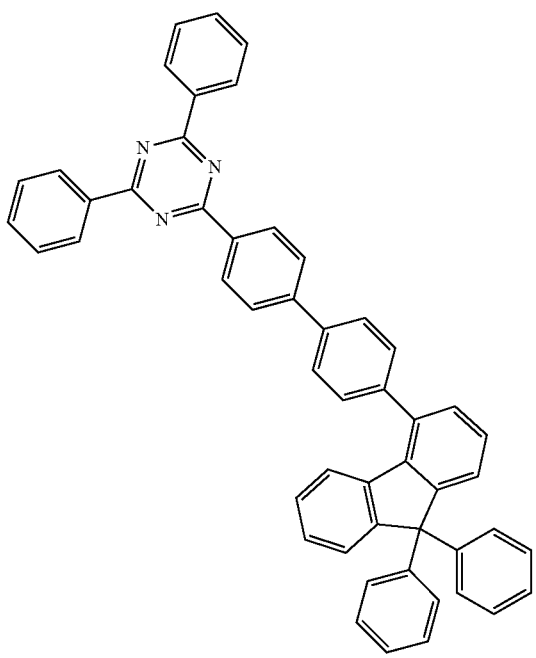
[Compound 68]
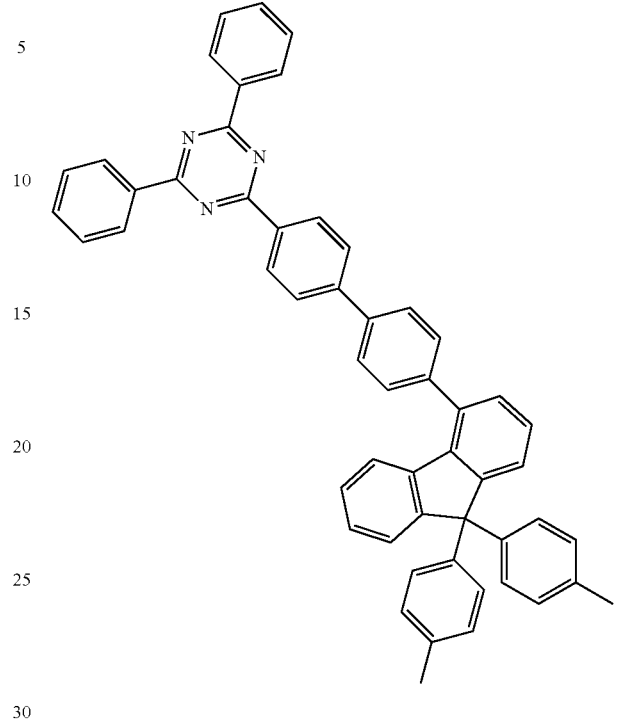
[Compound 69]
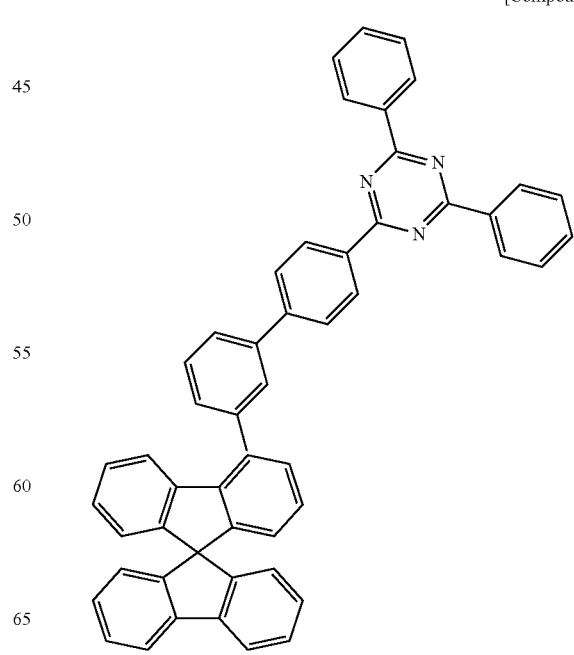

[Compound 70]
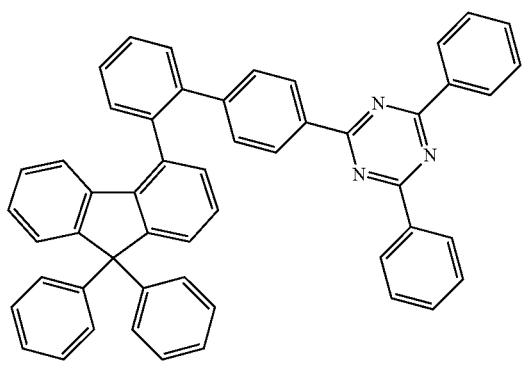
[Compound 71]
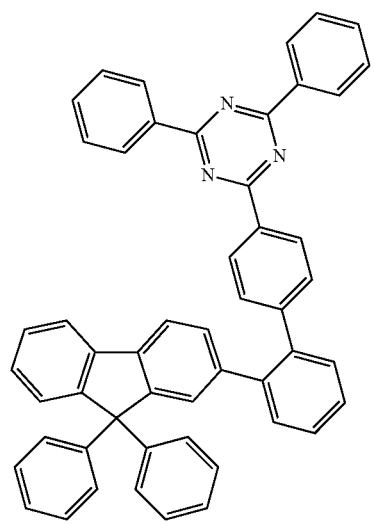
[Compound 72]
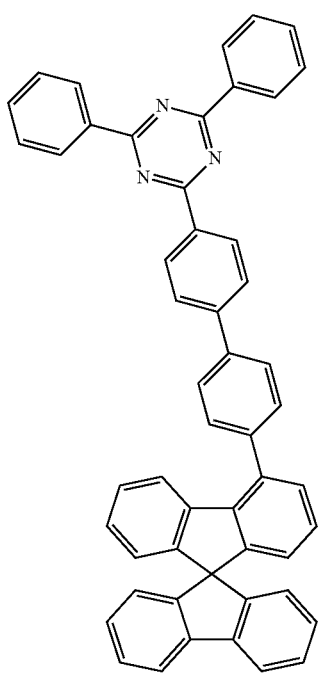
[Compound 73]
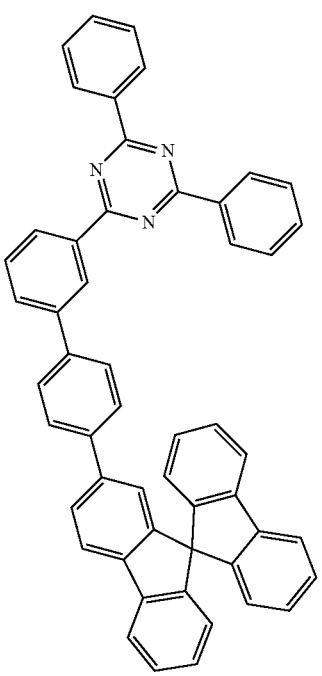
[Compound 74]
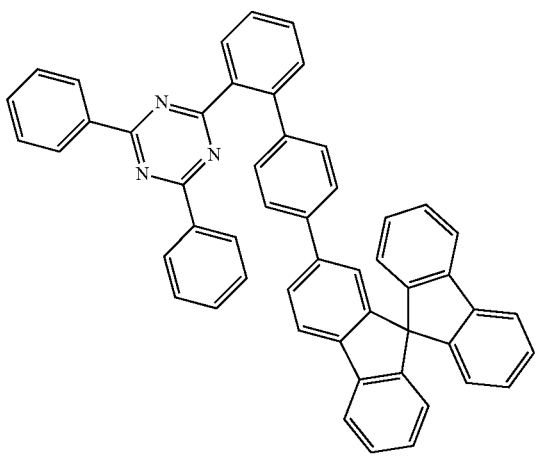

[Compound 75]
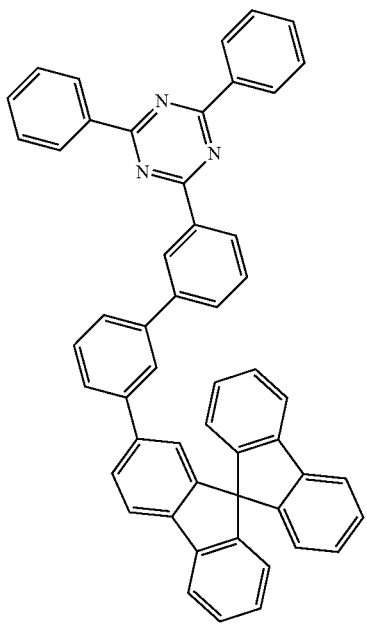
[Compound 76]
[Compound 78]
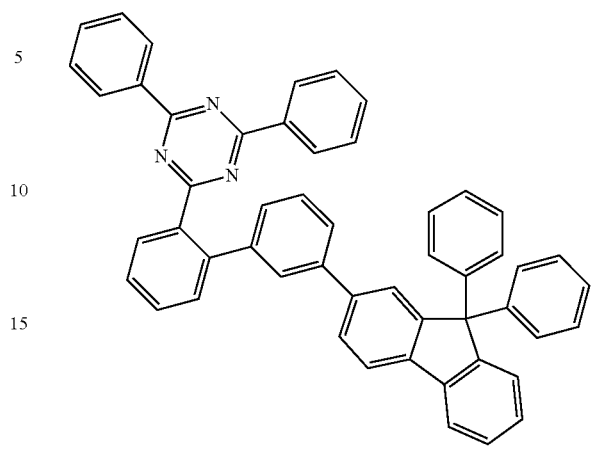
[Compound 79]
[Compound 80]
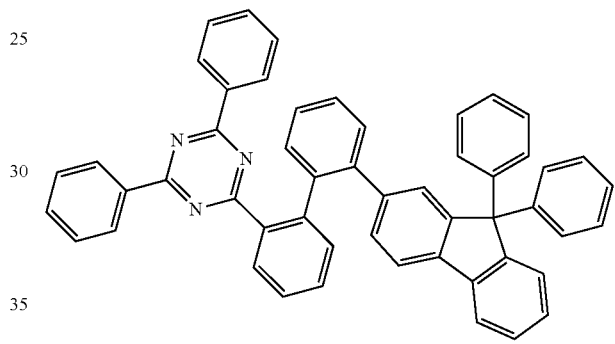
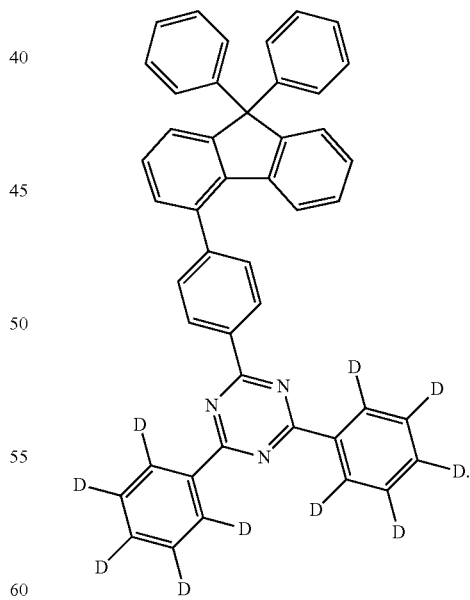
[Compound 77]
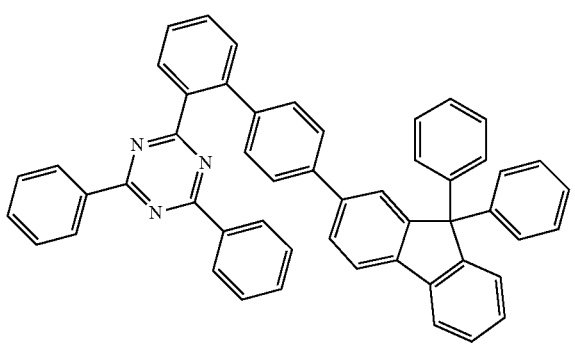
The compound represented by Formula 1 may be prepared based on the Preparation Examples to be described below. According to an exemplary embodiment, the compound may be prepared by the method such as the following Reaction Formula 1.

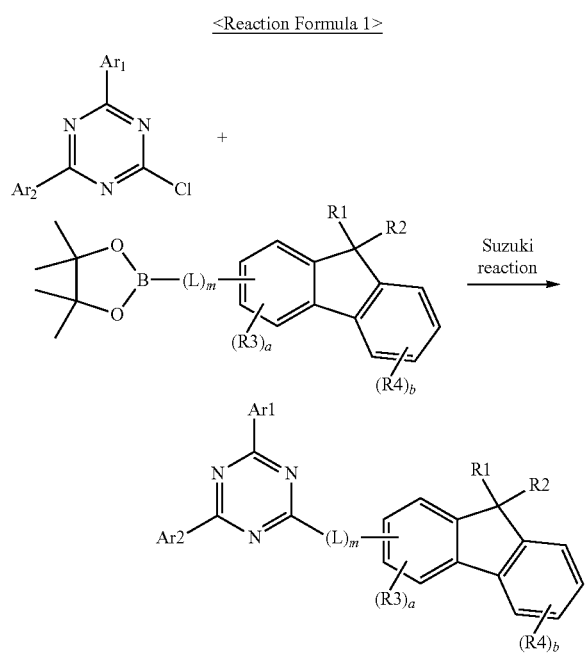

<Reaction Formula 1>

In Reaction Formula 1,
the definition of Ar1, Ar2, L, R1, R2, R3, R4, a, b, and m is the same as that in Formula 1.

Specifically, according to an exemplary embodiment of the present specification, the compound of Formula 1 may be prepared by coupling a compound of a triazine derivative substituted with halogen with an aromatic compound substituted with boronic acid or a boronic acid derivative using a palladium catalytic reaction.

Further, the present specification provides an organic light emitting device including the compound represented by any one of Formulae 1 to 8.

An exemplary embodiment of the present specification provides an organic light emitting device including: a first electrode; a second electrode provided to face the first electrode; and one or more organic material layers provided between the first electrode and the second electrode, in which one or more layers of the organic material layers includes the compound of any one of Formulae 1 to 8.

The organic material layer of the organic light emitting device of the present specification may also be composed of a single-layered structure, but may be composed of a multi-layered structure in which two or more organic material layers are stacked. For example, the organic light emitting device of the present invention may have a structure including a hole injection layer, a hole transporting layer, a light emitting layer, an electron transporting layer, an electron injection layer, and the like as organic material layers. However, the structure of the organic light emitting device is not limited thereto, and may include a fewer number of organic layers.

In an exemplary embodiment of the present specification, the organic material layer includes a hole injection layer, a hole transporting layer, or a layer which simultaneously transports and injects holes, and the hole injection layer, the hole transporting layer, or the layer which simultaneously transports and injects holes includes the compound of Formula 1.

In another exemplary embodiment, the organic material layer includes a light emitting layer, and the light emitting layer includes the compound of Formula 1.

According to an exemplary embodiment of the present specification, the organic material layer includes an electron transporting layer or an electron injection layer, and the electron transporting layer or the electron injection layer includes the compound of any one of Formulae 1 to 8.

In an exemplary embodiment of the present specification, the electron transporting layer, the electron injection layer, or the layer which simultaneously transports and injects electrons includes the compound of Formula 1.

In another exemplary embodiment, the organic material layer includes a light emitting layer and an electron transporting layer, and the electron transporting layer includes the compound of any one of Formulae 1 to 8.

In still another exemplary embodiment, the organic light emitting device may be an organic light emitting device having a structure (normal type) in which a positive electrode, one or more organic material layers, and a negative electrode are sequentially stacked on a substrate.

In yet another exemplary embodiment, the organic light emitting device may be an organic light emitting device having a reverse-direction structure (inverted type) in which a negative electrode, one or more organic material layers, and a positive electrode are sequentially stacked on a substrate.

Figure 2:
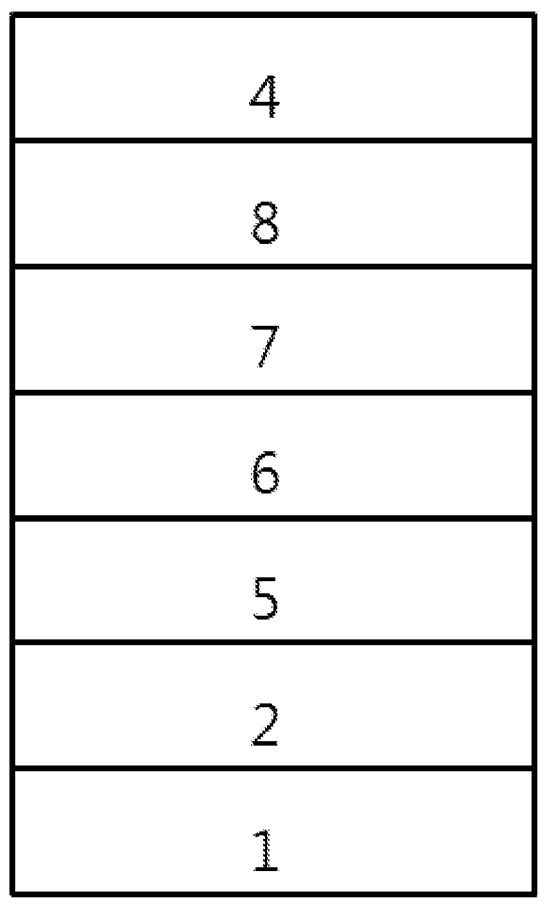
FIG. 2 illustrates an example of an organic light emitting device composed of a substrate 1, a positive electrode 2, a hole injection layer 5, a hole transporting layer 6, a light emitting layer 7, an electron transporting layer 8, and a negative electrode 4.
Figure 3:
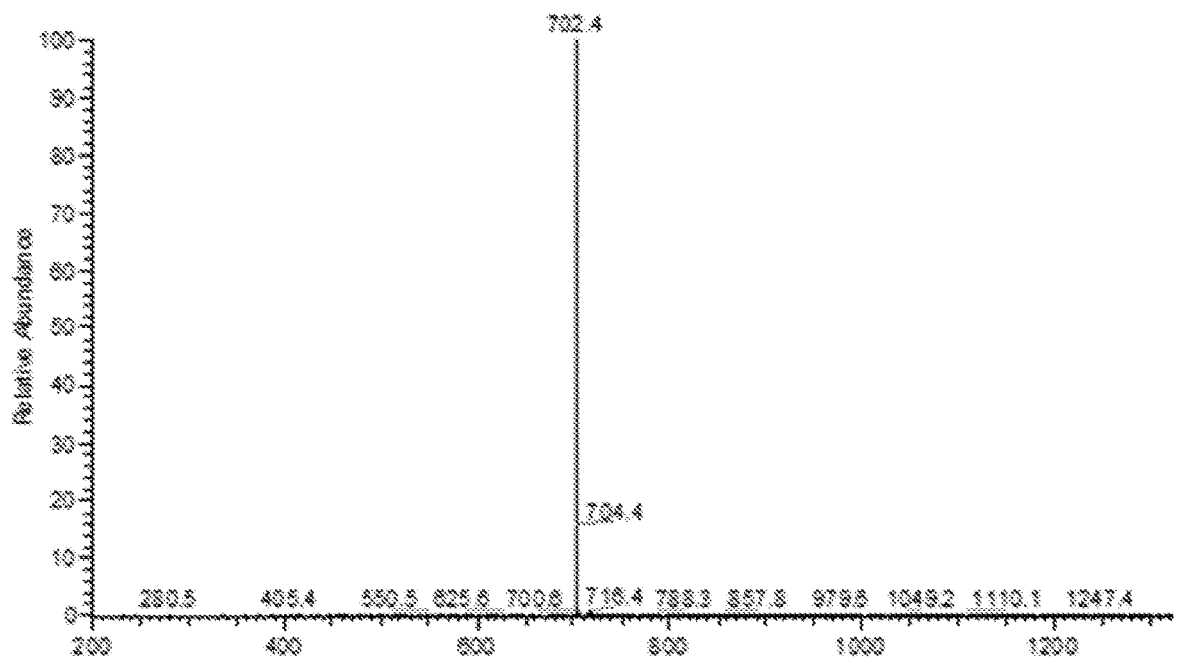
FIG. 3 illustrates an MS data result of Compound 67 prepared in the Examples.

For example, the structure of the organic light emitting device according to an exemplary embodiment of the present specification is illustrated in FIGS. 1 and 2.

FIG. 1 illustrates an example of an organic light emitting device composed of a substrate 1, a positive electrode 2, a light emitting layer 3, and a negative electrode 4. In the structure, the compound may be included in the light emitting layer.

FIG. 2 illustrates an example of an organic light emitting device composed of a substrate 1, a positive electrode 2, a hole injection layer 5, a hole transporting layer 6, a light emitting layer 7, an electron transporting layer 8, and a negative electrode 4. In the structure, the compound may be included in one or more layers of the hole injection layer, the hole transporting layer, the light emitting layer, and the electron transporting layer.

The organic light emitting device of the present specification may be manufactured by the materials and methods known in the art, except that one or more layers of the organic material layers include the compound of the present specification, that is, the compound of any one of Formulae 1 to 8.

When the organic light emitting device includes a plurality of organic material layers, the organic material layer may be formed of the same material or different materials.

One exemplary embodiment of the present specification is an organic light emitting device including: a first electrode; a second electrode provided to face the first electrode; a light emitting layer provided between the first electrode and the second electrode; and two or more organic material layers provided between the light emitting layer and the first electrode, or between the light emitting layer and the second electrode, in which at least one of the two or more organic material layers includes the hetero-cyclic compound. In one exemplary embodiment, as the two or more organic material layers, two or more may be selected from the group consisting of an electron transporting layer, an electron injection layer, a layer which simultaneously transports and injects electrons, and a hole blocking layer.

In an exemplary embodiment of the present specification, the organic material layer includes two or more electron transporting layers, and at least one of the two or more electron transporting layers includes the hetero-cyclic compound. Specifically, in an exemplary embodiment of the present specification, the hetero-cyclic compound may also be included in one layer of the two or more electron transporting layers, and may be included in each of the two or more electron transporting layers.

In addition, in an exemplary embodiment of the present specification, when the hetero-cyclic compound is included in each of the two or more electron transporting layers, the other materials except for the hetero-cyclic compound may be the same as or different from each other.

The organic light emitting device of the present specification may be manufactured by the materials and methods known in the art, except that one or more layers of the organic material layers include the compound of any one of Formulae 1 to 8, that is, the compound represented by any one of Formulae 1 to 8.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a positive electrode by using a physical vapor deposition (PVD) method such as sputtering or e-beam evaporation, forming an organic material layer including a hole injection layer, a hole transporting layer, a light emitting layer, and an electron transporting layer thereon, and then depositing a material, which may be used as a negative electrode, thereon. In addition to the method described above, an organic light emitting device may be made by subsequently depositing a negative electrode material, an organic material layer, and a positive electrode material on a substrate.

Further, the compound of any one of Formulae 1 to 8 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be manufactured by sequentially stacking a negative electrode material, an organic material layer, and a positive electrode material on a substrate (International Publication No. WO2003/012890). However, the manufacturing method is not limited thereto. In an exemplary embodiment of the present specification, the first electrode is a positive electrode, and the second electrode is a negative electrode.

In another exemplary embodiment, the first electrode is a negative electrode, and the second electrode is a positive electrode.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methylthiophene), poly[3,4-(ethylene-1,2-dioxy)thiophene] (PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or $LiO_2$/Al, and the like, but are not limited thereto.

The hole injection material is a layer which injects holes from an electrode, and is preferably a compound which has a capability of transporting holes, and thus has an effect of injecting holes at a positive electrode and an excellent effect of injecting holes for the light emitting layer or the light emitting material, prevents excitons produced from the light emitting layer from moving to an electron injection layer or an electron injection material, and is excellent in forming a thin film. It is preferred that the highest occupied molecular orbital (HOMO) of the hole injection material is between the work function of the positive electrode material and the HOMO of an adjacent organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The electron transporting layer is a layer which receives holes from the hole injection layer and transports holes to the light emitting layer, and a hole transporting material is suitably a material which may receive holes from a positive electrode or a hole injection layer to transfer holes to a light emitting layer, and has a large mobility for the holes. Specific examples thereof include an arylamine-based organic material, an electrically conductive polymer, a block copolymer in which a conjugate portion and a non-conjugate portion are present together, and the like, but are not limited thereto.

The light emitting material is a material which may receive holes and electrons from the hole transporting layer and the electron transporting layer, respectively, and combine the holes and the electrons to emit light in a visible ray region, and is preferably a material having good quantum efficiency to fluorescence or phosphorescence. Specific examples thereof include: an 8-hydroxyquinoline aluminum complex ($Alq_3$); a carbazole-based compound; a dimerized styryl compound; BAlq; a 10-hydroxybenzoquinoline-metal compound; a benzoxazole, benzothiazole and benzimidazole-based compound; a poly(p-phenylenevinylene (PPV)-based polymer; a spiro compound; polyfluorene, rubrene, and the like, but are not limited thereto.

The light emitting layer may include a host material and a dopant material. Examples of the host material include a condensed aromatic ring derivative, or a hetero ring-containing compound, and the like. Specifically, examples of the condensed aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a condensed aromatic ring derivative having a substituted or unsubstituted arylamino group, and examples thereof include a pyrene, an anthracene, a chrysene, a periflanthene, and the like having an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transporting layer is a layer which receives electrons from an electron injection layer and transports electrons to a light emitting layer, and an electron transporting material is a material which may receive electrons well from a negative electrode and may transfer electrons to a light emitting layer, and is suitably a material which has large mobility for the electrons. Specific examples thereof include: an Al complex of 8-hydroxyquinoline; a complex including $Alq_3$; an organic radical compound; and a hydroxyflavone-metal complex, but are not limited thereto. The electron transporting layer may be used with any desired cathode material, as used according to the related art. In particular, examples of an appropriate cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a negative electrode and an excellent effect of injecting electrons into a light emitting layer or a light emitting material, prevents excitons produced from the light emitting layer from moving to the hole injection layer, and is also excellent in forming a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone and derivatives thereof, a metal complex compound, a nitrogen-containing 5-membered derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris (2-methyl-8-hydroxyquinolinato) aluminum, tris(8-hydroxyquinolinato) gallium, bis(10-hydroxybenzo[h] quinolinato) beryllium, bis(10-hydroxybenzo[h] quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The organic light emitting device according to the present specification may be a top emission type, a bottom emission type, or a dual emission type according to the material to be used.

In an exemplary embodiment of the present specification, the compound of Formula 1 may be included in an organic solar cell or an organic transistor in addition to the organic light emitting device.

The preparation of the compound represented by Formula 1 and the organic light emitting device including the same will be specifically described in the following Examples. However, the following Examples are provided for illustrating the present specification, and the range of the present specification is not limited thereby.

PREPARATION EXAMPLES

<Preparation Example 1> Preparation of [Compound 1]

2-chloro-4,6-diphenyl-1,3,5-triazine (10.0 g, 37.4 mmol) and 2-(4-(9,9-diphenyl-9H-fluoren-2-yl)phenyl)-4,4,5,5-tetramethyl-1,3,2-ioxaborolane (19.4 g, 37.4 mmol) were put into 150 mL of THF. 75 mL of 2.0 M $K_2CO_3$ and 0.8 g of $Pd(PPh_3)_4$ were put thereinto, and then the resulting mixture was stirred and refluxed for 5 hours. The mixture was cooled to normal temperature, and then a solid produced by filtering the mixture was recrystallized with chloroform and ethanol, thereby preparing [Compound 1]. (19.9 g, yield 85%, MS: $[M+H]^+$=626)

<Preparation Example 2> Preparation of [Compound 2]

2-chloro-4,6-diphenyl-1,3,5-triazine (10.0 g, 37.4 mmol) and 2-(4-(9,9'-spirobi[fluoren]-2-yl)phenyl)-4,4,5,5-tetramethyl-1,3,2-dioxaborolane (19.4 g, 37.4 mmol) were put into 150 mL of THF. 75 mL of 2.0 M $K_2CO_3$ and 0.8 g of $Pd(PPh_3)_4$ were put thereinto, and then the resulting mixture was stirred and refluxed for 6 hours. The mixture was cooled to normal temperature, and then a solid produced by filtering the mixture was recrystallized with chloroform and ethanol, thereby preparing [Compound 2]. (18.7 g, yield 80%, MS: $[M+H]^+$=624)

<Preparation Example 3> Preparation of [Compound 3]

2-chloro-4,6-diphenyl-1,3,5-triazine (10.0 g, 37.4 mmol) and 2-(4-(9,9-diphenyl-9H-fluoren-4-yl)phenyl)-4,4,5,5-tetramethyl-1,3,2-dioxaborolane (19.4 g, 37.4 mmol) were put into 150 mL of THF. 75 mL of 2.0 M $K_2CO_3$ and 0.8 g of $Pd(PPh_3)_4$ were put thereinto, and then the resulting mixture was stirred and refluxed for 6 hours. The mixture was cooled to normal temperature, and then a solid produced by filtering the mixture was recrystallized with chloroform and ethanol, thereby preparing [Compound 3]. (18.0 g, yield 77%, MS: $[M+H]^+$=626)

<Preparation Example 4> Preparation of [Compound 5]

2-chloro-4,6-diphenyl-1,3,5-triazine (10.0 g, 37.4 mmol) and 2-(3-(9,9-diphenyl-9H-fluoren-2-yl)phenyl)-4,4,5,5-tetramethyl-1,3,2-dioxaborolane (19.4 g, 37.4 mmol) were put into 150 mL of THF. 75 mL of 2.0 M $K_2CO_3$ and 0.8 g of $Pd(PPh_3)_4$ were put thereinto, and then the resulting mixture was stirred and refluxed for 7 hours. The mixture was cooled to normal temperature, and then a solid produced by filtering the mixture was recrystallized with chloroform and ethanol, thereby preparing [Compound 5]. (16.9 g, yield 72%, MS: $[M+H]^+$=626)

<Preparation Example 5> Preparation of [Compound 7]

2-chloro-4,6-diphenyl-1,3,5-triazine (10.0 g, 37.4 mmol) and 2-(2-(9,9-diphenyl-9H-fluoren-2-yl)phenyl)-4,4,5,5-tetramethyl-1,3,2-dioxaborolane (19.4 g, 37.4 mmol) were put into 150 mL of THF. 75 mL of 2.0 M K$_2$CO$_3$ and 0.8 g of Pd(PPh$_3$)$_4$ were put thereinto, and then the resulting mixture was stirred and refluxed for 5 hours. The mixture was cooled to normal temperature, and then a solid produced by filtering the mixture was recrystallized with chloroform and ethanol, thereby preparing [Compound 7]. (17.8 g, yield 76%, MS: [M+H]$^+$=626)

<Preparation Example 6> Preparation of [Compound 13]

2,4-di([1,1'-biphenyl]-4-yl)-6-chloro-1,3,5-triazine (10.0 g, 23.8 mmol) and 2-(4-(9,9-dimethyl-9H-fluoren-2-yl)phenyl)-4,4,5,5-tetramethyl-1,3,2-dioxaborolane (9.4 g, 23.8 mmol) were put into 100 mL of THF. 50 mL of 2.0 M K$_2$CO$_3$ and 0.5 g of Pd(PPh$_3$)$_4$ were put thereinto, and then the resulting mixture was stirred and refluxed for 5 hours. The mixture was cooled to normal temperature, and then a solid produced by filtering the mixture was recrystallized with chloroform and ethanol, thereby preparing [Compound 13]. (12.3 g, yield 79%, MS: [M+H]$^+$=654)

<Preparation Example 7> Preparation of [Compound 27]

2-chloro-4,6-di(naphthalen-1-yl)-1,3,5-triazine (10.0 g, 27.2 mmol) and 2-(4-(9,9-diphenyl-9H-fluoren-4-yl)phenyl)-4,4,5,5-tetramethyl-1,3,2-dioxaborolane (14.7 g, 27.2 mmol) were put into 150 mL of THF. 75 mL of 2.0 M K$_2$CO$_3$ and 0.6 g of Pd(PPh$_3$)$_4$ were put thereinto, and then the resulting mixture was stirred and refluxed for 6 hours. The mixture was cooled to normal temperature, and then a solid produced by filtering the mixture was recrystallized with chloroform and ethanol, thereby preparing [Compound 27]. (13.8 g, yield 70%, MS: [M+H]$^+$=726)

<Preparation Example 8> Preparation of [Compound 32]

2-chloro-4,6-di(naphthalen-2-yl)-1,3,5-triazine (10.0 g, 27.2 mmol) and 2-(4-(9,9'-spirobi[fluoren]-4-yl)phenyl)-4,4,5,5-tetramethyl-1,3,2-dioxaborolane (14.1 g, 27.2 mmol) were put into 150 mL of THF. 75 mL of 2.0 M K$_2$CO$_3$ and 0.6 g of Pd(PPh$_3$)$_4$ were put thereinto, and then the resulting mixture was stirred and refluxed for 7 hours. The mixture was cooled to normal temperature, and then a solid produced by filtering the mixture was recrystallized with chloroform and ethanol, thereby preparing [Compound 32]. (15.0 g, yield 76%, MS: [M+H]$^+$=724)

<Preparation Example 9> Preparation of [Compound 36]

2-chloro-4,6-di(phenanthren-9-yl)-1,3,5-triazine (10.0 g, 21.4 mmol) and 2-(4-(9,9-dimethyl-9H-fluoren-1-yl)phenyl)-4,4,5,5-tetramethyl-1,3,2-dioxaborolane (8.5 g, 21.4 mmol) were put into 150 mL of THF. 75 mL of 2.0 M K$_2$CO$_3$ and 0.5 g of Pd(PPh$_3$)$_4$ were put thereinto, and then the resulting mixture was stirred and refluxed for 5 hours. The mixture was cooled to normal temperature, and then a solid produced by filtering the mixture was recrystallized with chloroform and ethanol, thereby preparing [Compound 36]. (11.6 g, yield 77%, MS: [M+H]$^+$=702)

<Preparation Example 10> Preparation of [Compound 46]

2-chloro-4,6-diphenyl-1,3,5-triazine (10.0 g, 37.4 mmol) and 2-(4'-(9,9-diphenyl-9H-fluoren-2-yl)-[1,1'-biphenyl]-4-yl)-4,4,5,5-tetramethyl-1,3,2-dioxaborolane (22.3 g, 37.4 mmol) were put into 150 mL of THF. 75 mL of 2.0 M K$_2$CO$_3$ and 0.8 g of Pd(PPh$_3$)$_4$ were put thereinto, and then the resulting mixture was stirred and refluxed for 6 hours. The mixture was cooled to normal temperature, and then a solid produced by filtering the mixture was recrystallized with chloroform and ethanol, thereby preparing [Compound 46]. (17.9 g, yield 68%, MS: [M+H]$^+$=702)

<Preparation Example 11> Preparation of [Compound 47]

2-chloro-4,6-diphenyl-1,3,5-triazine (10.0 g, 37.4 mmol) and 2-(4'-(9,9'-spirobi[fluoren]-2-yl)-[1,1'-biphenyl]-4-yl)-4,4,5,5-tetramethyl-1,3,2-dioxaborolane (22.2 g, 37.4 mmol) were put into 150 mL of THF. 75 mL of 2.0 M K$_2$CO$_3$ and 0.8 g of Pd(PPh$_3$)$_4$ were put thereinto, and then the resulting mixture was stirred and refluxed for 8 hours. The mixture was cooled to normal temperature, and then a solid produced by filtering the mixture was recrystallized with chloroform and ethanol, thereby preparing [Compound 47]. (21.2 g, yield 81%, MS: [M+H]$^+$=700)

<Preparation Example 12> Preparation of [Compound 67]

2-chloro-4,6-diphenyl-1,3,5-triazine (10.0 g, 37.4 mmol) and 2-(4'-(9,9-diphenyl-9H-fluoren-4-yl)-[1,1'-biphenyl]-4-yl)-4,4,5,5-tetramethyl-1,3,2-dioxaborolane (22.3 g, 37.4 mmol) were put into 150 mL of THF. 75 mL of 2.0 M K$_2$CO$_3$ and 0.8 g of Pd(PPh$_3$)$_4$ were put thereinto, and then the resulting mixture was stirred and refluxed for 8 hours. The mixture was cooled to normal temperature, and then a solid produced by filtering the mixture was recrystallized with chloroform and ethanol, thereby preparing [Compound 67]. (18.6 g, yield 71%, MS: [M+H]$^+$=702)

<Preparation Example 13> Preparation of [Compound 80]

2-chloro-4,6-bis(phenyl-d5)-1,3,5-triazine (10.0 g, 36.0 mmol) and 2-(4-(9,9-diphenyl-9H-fluoren-4-yl)phenyl)-4,4,5,5-tetramethyl-1,3,2-dioxaborolane (18.7 g 36.0 mmol) were put into 150 mL of THF. 75 mL of 2.0 M K$_2$CO$_3$ and 0.8 g of Pd(PPh$_3$)$_4$ were put thereinto, and then the resulting mixture was stirred and refluxed for 6 hours. The mixture was cooled to normal temperature, and then a solid produced by filtering the mixture was recrystallized with chloroform and ethanol, thereby preparing [Compound 80]. (16.0 g, yield 70%, MS: [M+H]$^+$=636)

EXAMPLE

Example 1

A glass substrate thinly coated with indium tin oxide (ITO) to have a thickness of 500 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was conducted twice using distilled water for 10 minutes. After the washing using distilled water was completed, ultrasonic washing was conducted using isopropyl alcohol, acetone, and methanol solvents, and drying was conducted, and then the product was transported to a plasma washing machine. In addition, the substrate was washed using oxygen plasma for 5 minutes, and then transported to a vacuum evaporator.

The following Compound [HI-A] was thermally vacuum deposited to a thickness of 600 Å on the transparent ITO electrode, which was prepared as described above, thereby forming a hole injection layer. Compound [HAT] (50 Å) and the following Compound [HT-A] (600 Å) were sequentially vacuum deposited on the hole injection layer, thereby forming a hole transporting layer.

Subsequently, the following Compounds [BH] and [BD] were vacuum deposited at a weight ratio of 25:1 to have a film thickness of 200 Å on the hole transporting layer, thereby forming a light emitting layer.

[Compound 1] and the following Compound [LiQ] (lithium quinolate) were vacuum deposited at a weight ratio of 1:1 on the light emitting layer, thereby forming an electron injection and transporting layer having a thickness of 350 Å. Lithium fluoride (LiF) and aluminum were subsequently deposited to have a thickness of 10 Å and 1,000 Å, respectively, on the electron injection and transporting layer, thereby forming a negative electrode.

In the aforementioned procedure, the deposition rate of the organic material was maintained at 0.4 to 0.9 Å/sec, the deposition rates of lithium fluoride and aluminum of the negative electrode were maintained at 0.3 Å/sec, and at 2 Å/sec, respectively, and the degree of vacuum during the deposition was maintained at $1\times10^{-7}$ to $5\times10^{-8}$ torr, thereby manufacturing an organic light emitting device.

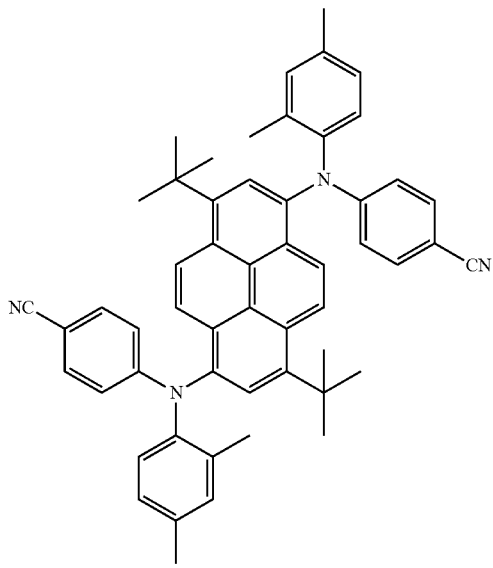
[BD]

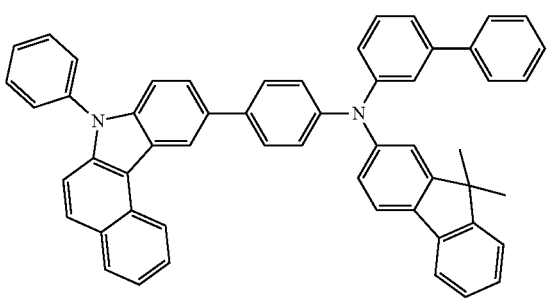
[HT-A]

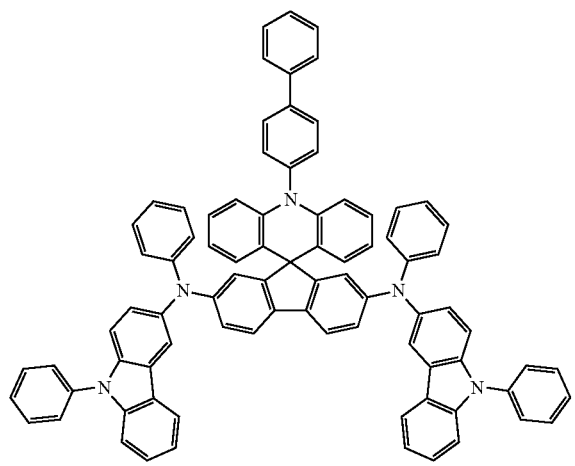
[HI-A]

[BH]

[LiQ]

-continued

[ET-A]

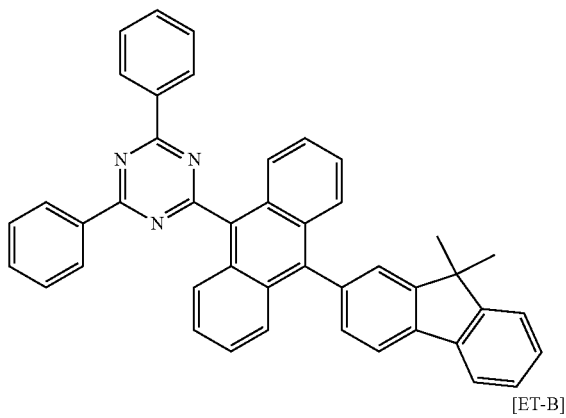

[ET-B]

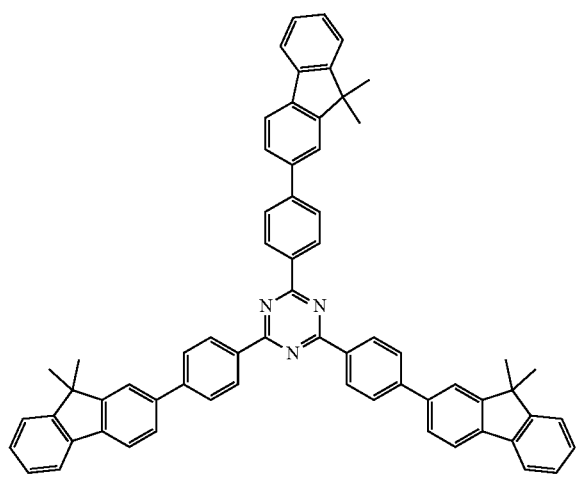

Example 2

An organic light emitting device was manufactured in the same manner as in [Example 1], except that [Compound 2] was used instead of [Compound 1] of [Example 1].

Example 3

An organic light emitting device was manufactured in the same manner as in [Example 1], except that [Compound 3] was used instead of [Compound 1] of [Example 1].

Example 4

An organic light emitting device was manufactured in the same manner as in [Example 1], except that [Compound 5] was used instead of [Compound 1] of [Example 1].

Example 5

An organic light emitting device was manufactured in the same manner as in [Example 1], except that [Compound 7] was used instead of [Compound 1] of [Example 1].

Example 6

An organic light emitting device was manufactured in the same manner as in [Example 1], except that [Compound 13] was used instead of [Compound 1] of [Example 1].

Example 7

An organic light emitting device was manufactured in the same manner as in [Example 1], except that [Compound 27] was used instead of [Compound 1] of [Example 1].

Example 8

An organic light emitting device was manufactured in the same manner as in [Example 1], except that [Compound 32] was used instead of [Compound 1] of [Example 1].

Example 9

An organic light emitting device was manufactured in the same manner as in [Example 1], except that [Compound 36] was used instead of [Compound 1] of [Example 1].

Example 10

An organic light emitting device was manufactured in the same manner as in [Example 1], except that [Compound 46] was used instead of [Compound 1] of [Example 1].

Example 11

An organic light emitting device was manufactured in the same manner as in [Example 1], except that [Compound 47] was used instead of [Compound 1] of [Example 1].

Example 12

An organic light emitting device was manufactured in the same manner as in [Example 1], except that [Compound 67] was used instead of [Compound 1] of [Example 1].

Example 13

An organic light emitting device was manufactured in the same manner as in [Example 1], except that [Compound 80] was used instead of [Compound 1] of [Example 1].

Comparative Example 1

An organic light emitting device was manufactured in the same manner as in [Example 1], except that [ET-A] was used instead of [Compound 1] of [Example 1].

Comparative Example 2

An organic light emitting device was manufactured in the same manner as in [Example 1], except that [ET-B] was used instead of [Compound 1] of [Example 1].

For the organic light emitting devices manufactured by the above-described method, the driving voltage and the light emitting efficiency were measured at a current density of 10 mA/cm$^2$, and a time ($T_{90}$) for reaching a 90% value compared to the initial luminance was measured at a current density of 20 mA/cm$^2$. The results are shown in the following Table 1.

TABLE 1

|  | Voltage (V) | Efficiency (Cd/A) | Color Coordinate (x, y) | Service life (h) $T_{90}$ at 20 mA/cm² |
| --- | --- | --- | --- | --- |
| Example 1 | 4.70 | 4.81 | (0.143, 0.107) | 165 |
| Example 2 | 4.65 | 4.63 | (0.144, 0.106) | 180 |
| Example 3 | 4.45 | 5.02 | (0.143, 0.106) | 185 |
| Example 4 | 4.66 | 4.91 | (0.144, 0.107) | 152 |
| Example 5 | 4.51 | 4.82 | (0.143, 0.106) | 172 |
| Example 6 | 4.77 | 5.01 | (0.144, 0.106) | 192 |
| Example 7 | 4.41 | 5.15 | (0.143, 0.107) | 155 |
| Example 8 | 4.47 | 4.93 | (0.143, 0.106) | 167 |
| Example 9 | 4.72 | 4.66 | (0.143, 0.106) | 169 |
| Example 10 | 4.66 | 4.84 | (0.144, 0.107) | 176 |
| Example 11 | 4.72 | 4.73 | (0.144, 0.106) | 188 |
| Example 12 | 4.51 | 5.02 | (0.144, 0.106) | 182 |
| Example 13 | 4.47 | 4.97 | (0.143, 0.106) | 178 |
| Comparative Example 1 | 5.57 | 3.58 | (0.144, 0.108) | 122 |
| Comparative Example 2 | 5.14 | 4.12 | (0.143, 0.109) | 135 |

From the result of the table, the compound represented by Formula 1 according to the present invention may be used for an organic layer of the organic light emitting device which may simultaneously inject and transport electrons. The organic light emitting device using the same has low driving voltage and high efficiency, and may improve stability of the device by hole stability of the compound.

In particular, the compound represented by Formula 1 according to the present invention is excellent in thermal stability, and may be used in a mixture with an n-type dopant when used in the organic layer which simultaneously injects and transports electrons.

Furthermore, according to an exemplary embodiment of the present specification, the case where the compound represented by Formula 8 is used for an organic light emitting device has a lower driving voltage and/or a higher efficiency than the case where the compounds represented by Formulae 5 to 7 are used for an organic light emitting device, and stability of the device may be increased by the hole stability of the compound.

EXPLANATION OF REFERENCE NUMERALS AND SYMBOLS

1: Substrate
2: Positive electrode
3: Light emitting layer
4: Negative electrode
5: Hole injection layer
6: Hole transporting layer
7: Light emitting layer
8: Electron transporting layer

The invention claimed is:

1. A compound of Formula 1:

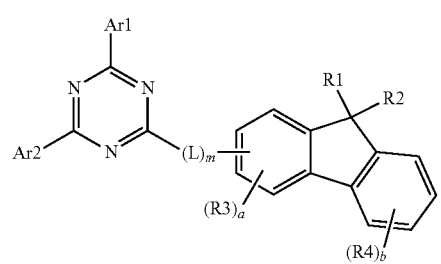

<Formula 1> wherein in Formula 1:

the

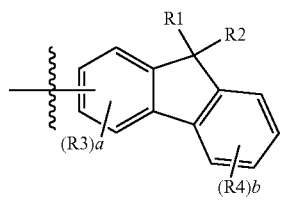

moiety is any one selected from among the following structures:

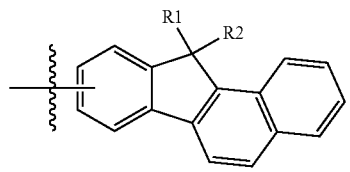

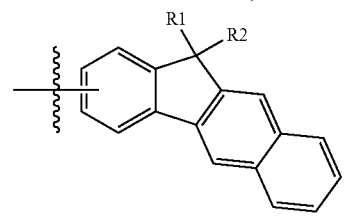

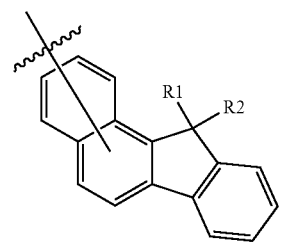

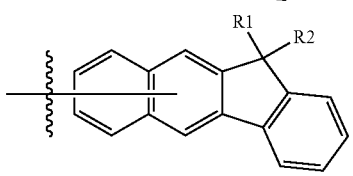

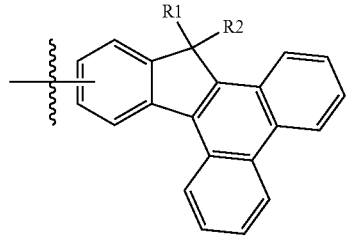

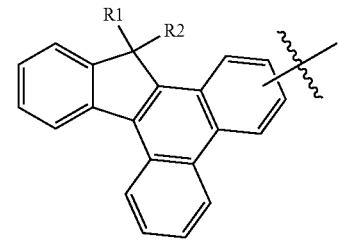

-continued

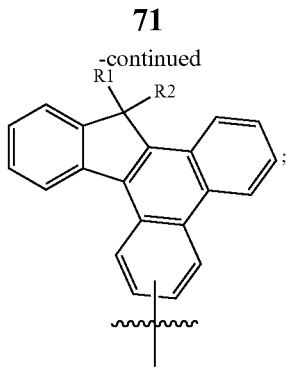

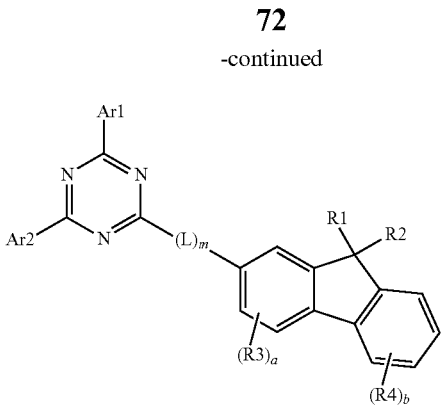

<Formula 6>

(a) R1 and R2 are the same as or different from each other, and each independently is hydrogen, deuterium, a halogen group, a substituted or unsubstituted alkyl group, a substituted or unsubstituted alkoxy group, a substituted or unsubstituted thioalkoxy group, a substituted or unsubstituted cyclic alkyl group, a substituted or unsubstituted alkenyl group, a substituted or unsubstituted alkoxy group, a substituted or unsubstituted thioalkoxy group, a substituted or unsubstituted aryl group, a substituted or unsubstituted hetero-cyclic group, a substituted or unsubstituted aryloxy group, or a substituted or unsubstituted heteroaryloxy group, or (b) R1 and R2 combine with each other to form a substituted or unsubstituted ring;

Ar1 and Ar2 are the same as or different from each other, and each independently is a substituted or unsubstituted aryl group or a substituted or unsubstituted heteroaryl group;

L is a substituted or unsubstituted arylene, or a substituted or unsubstituted heteroarylene;

m is an integer of 1 to 5; and when m is 2 or more, the Ls are the same as or different from each other.

2. The compound of claim 1, wherein Ar1 and Ar2 are each independently a substituted or unsubstituted aryl group.

3. The compound of claim 1, wherein Formula 1 is any one of the following Formulae 5 to 8:

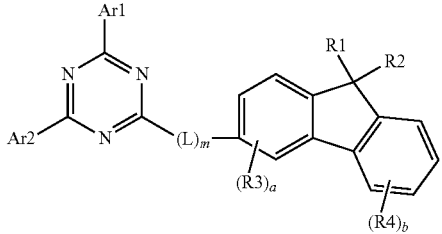

<Formula 7>

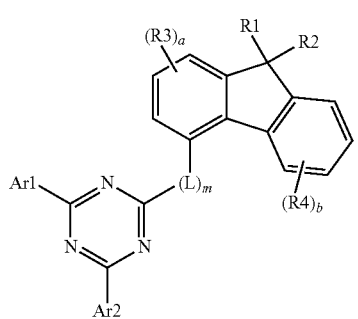

<Formula 8> wherein:

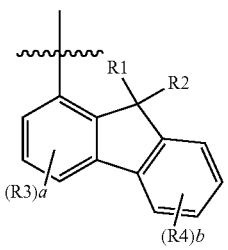

the

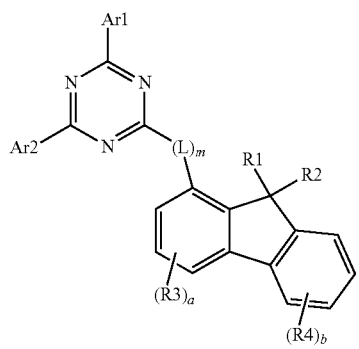

<Formula 5>

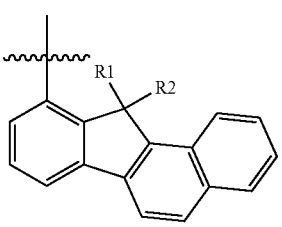

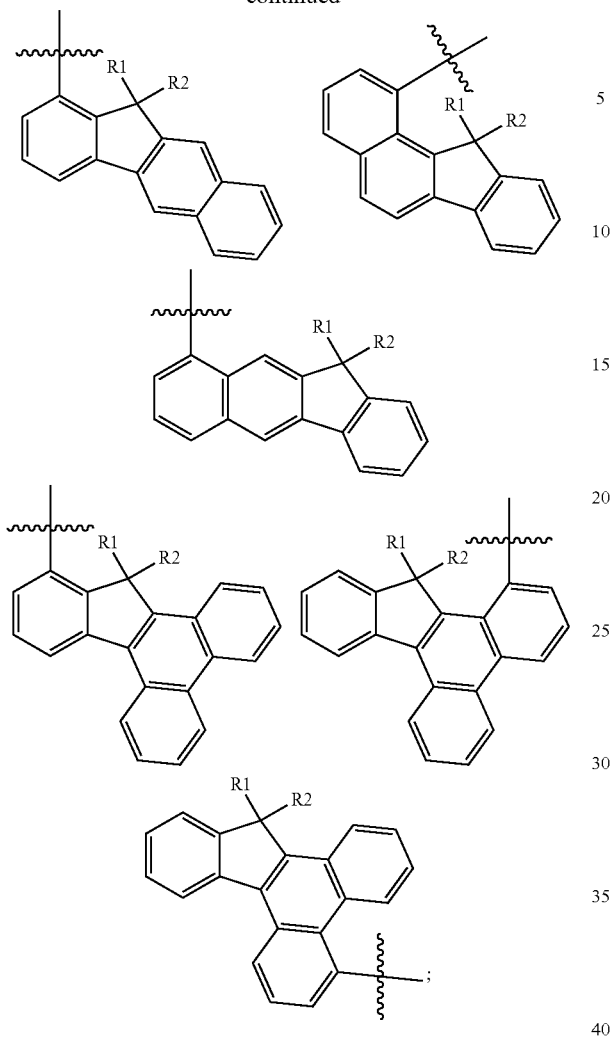
the moiety is any one selected from among the following structures:
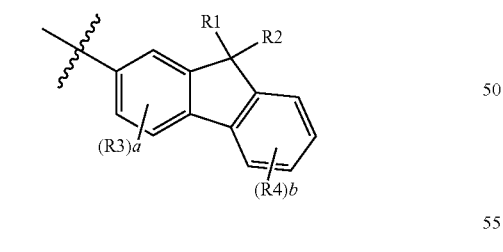
the moiety is any one selected from among the following structures:
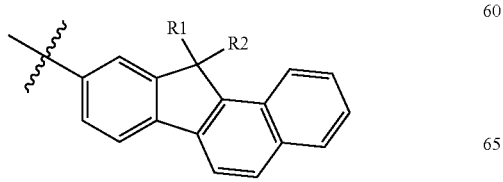
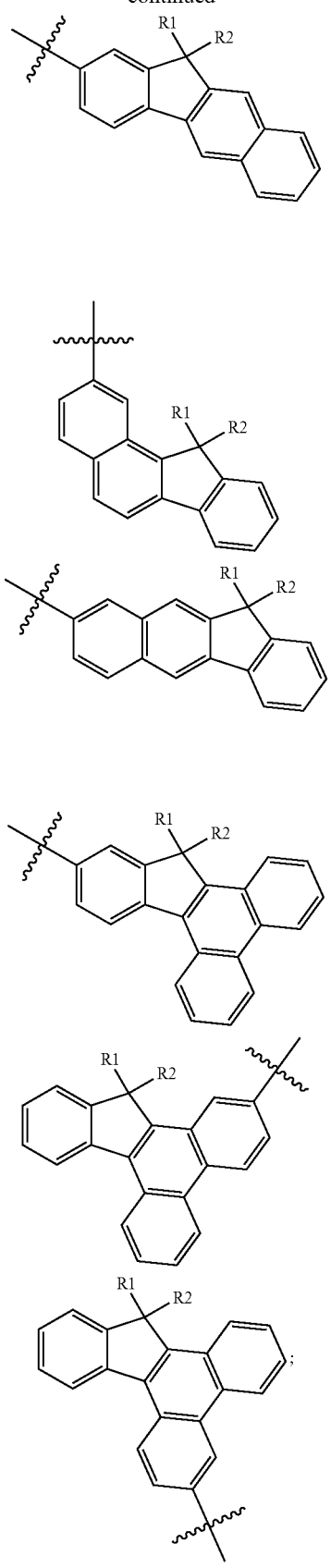

the
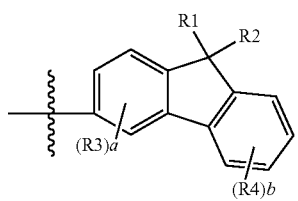
moiety is any one selected from among the following structures:
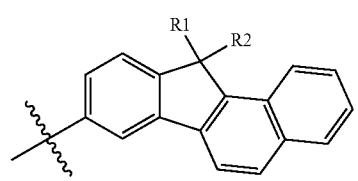
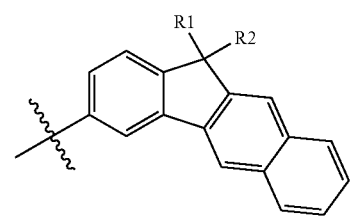
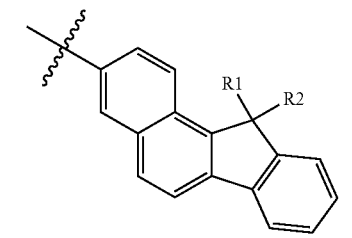
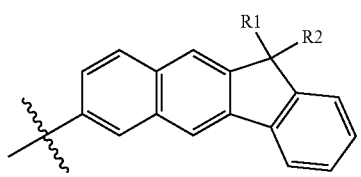
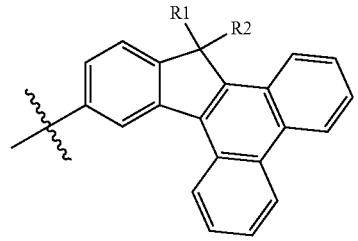
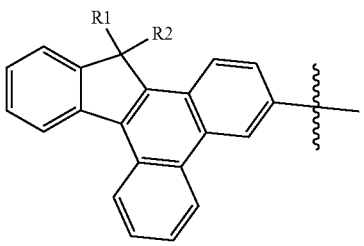
-continued
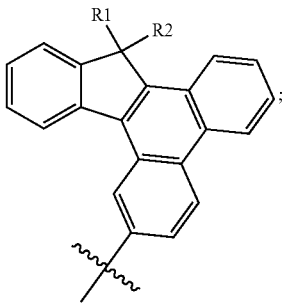
the
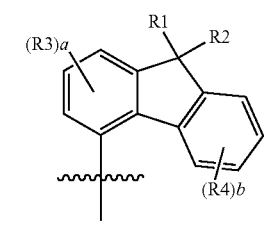
moiety is any one selected from among the following structures:
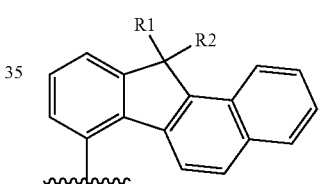 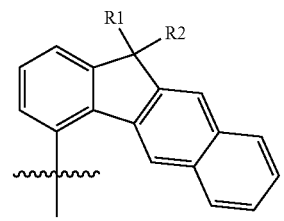
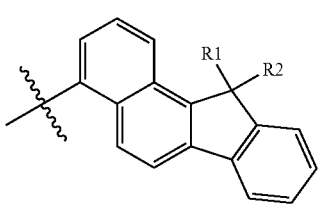
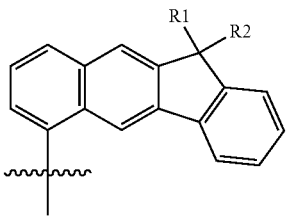
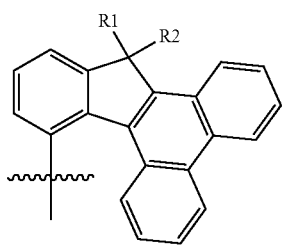

-continued

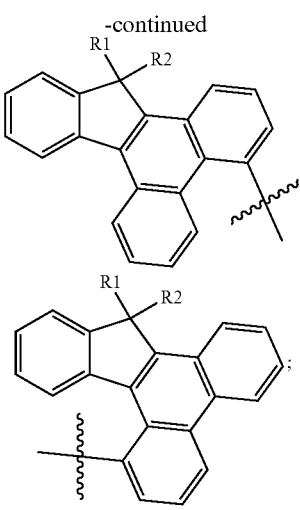

and
the definition of each of Ar1, Ar2, R1 R2, L, and m is the same as defined in Formula 1.

4. The compound of claim 1, wherein:
R1 is

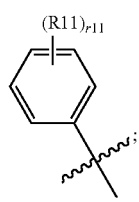

R2 is

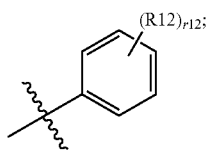

R11 and R12 are the same as or different from each other, and each independently is hydrogen, deuterium, a halogen group, a nitrile group, a nitro group, a hydroxy group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted aryl sulfoxy group, a substituted or unsubstituted alkenyl group, a substituted or unsubstituted silyl group, a substituted or unsubstituted boron group, a substituted or unsubstituted aryl group, or a substituted or unsubstituted hetero-cyclic group, or two or more adjacent groups combine with each other to form a substituted or unsubstituted ring;
r11 and r12 are the same as or different from each other, and each independently is an integer of 0 to 5; and
when r11 and r12 are each 2 or more, the structures in the parenthesis are the same as or different from each other.

5. The compound of claim 1, wherein L is any one selected from among the following structures:

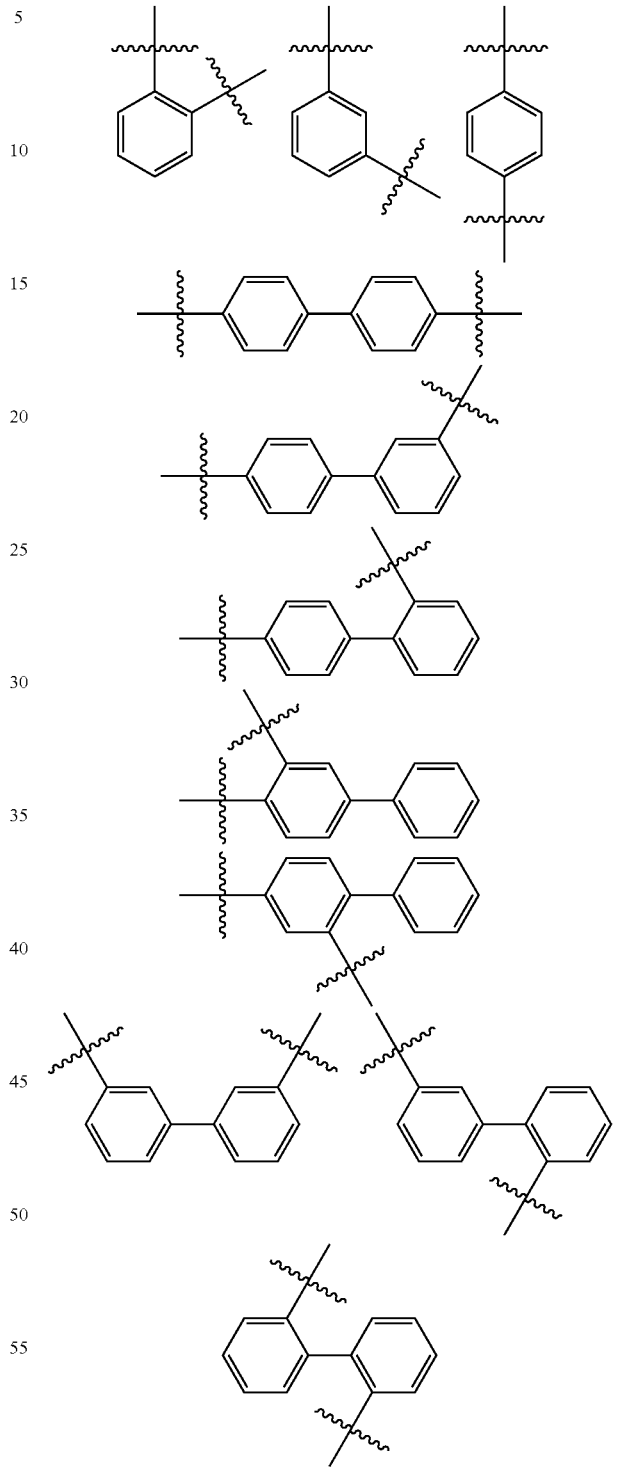

wherein the structures are unsubstituted or substituted with one or more substituents selected from the group consisting of deuterium, a halogen group, a nitrile group, nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group.

6. The compound of claim 1, wherein Ar1 and Ar2 are the same as or different from each other, and each independently is a substituted or unsubstituted phenyl group, a substituted or unsubstituted naphthyl group, a substituted or unsubstituted biphenyl group, a substituted or unsubstituted terphenyl group, a substituted or unsubstituted anthracenyl group, a substituted or unsubstituted phenanthryl group, a substituted or unsubstituted pyrenyl group, a substituted or unsubstituted perylenyl group, a substituted or unsubstituted chrysenyl group, a substituted or unsubstituted fluorenyl group, or a substituted or unsubstituted heteroaryl group.

7. The compound of claim 1, wherein Ar1 and Ar2 are the same as or different from each other, and each independently is a substituted or unsubstituted naphthyl group.

8. The compound of claim 7, wherein R1 and R2 are the same as or different from each other, and each independently is a methyl group or a phenyl group, or combine with each other to form a ring.

9. The compound of claim 1, wherein the

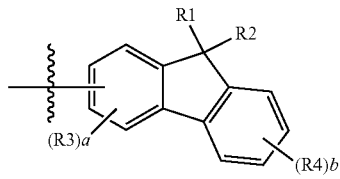

moiety is

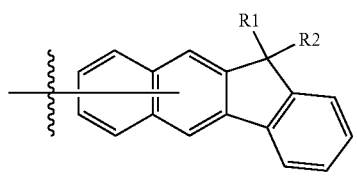

10. An organic light emitting device comprising:
an anode;
a cathode; and
one or more organic material layers provided between the anode and the cathode,
wherein one or more of the one or more organic material layers comprise the compound of claim 1.

11. The organic light emitting device of claim 10, wherein the one or more organic material layers comprising the compound is one or two or more layers selected from the group consisting of an electron transporting layer, an electron injection layer, a layer which simultaneously injects or transports electrons, and an electron controlling layer.

12. The organic light emitting device of claim 11, wherein the one or more organic material layers comprising the compound comprises the compound as a host and an n-type dopant as a dopant.

13. The organic light emitting device of claim 12, wherein the n-type dopant comprises an alkali metal, an alkali metal compound, an alkaline earth metal, an alkaline earth metal compound, or a combination thereof.

14. The organic light emitting device of claim 12, wherein the n-type dopant comprises one or two or more selected from the group consisting of Li, Na, K, Rb, Cs, Mg, Ca, Sr, Ba, La, Nd, Sm, Eu, Tb, Yb, LiF, Li$_2$O, CsF, and the following compounds:

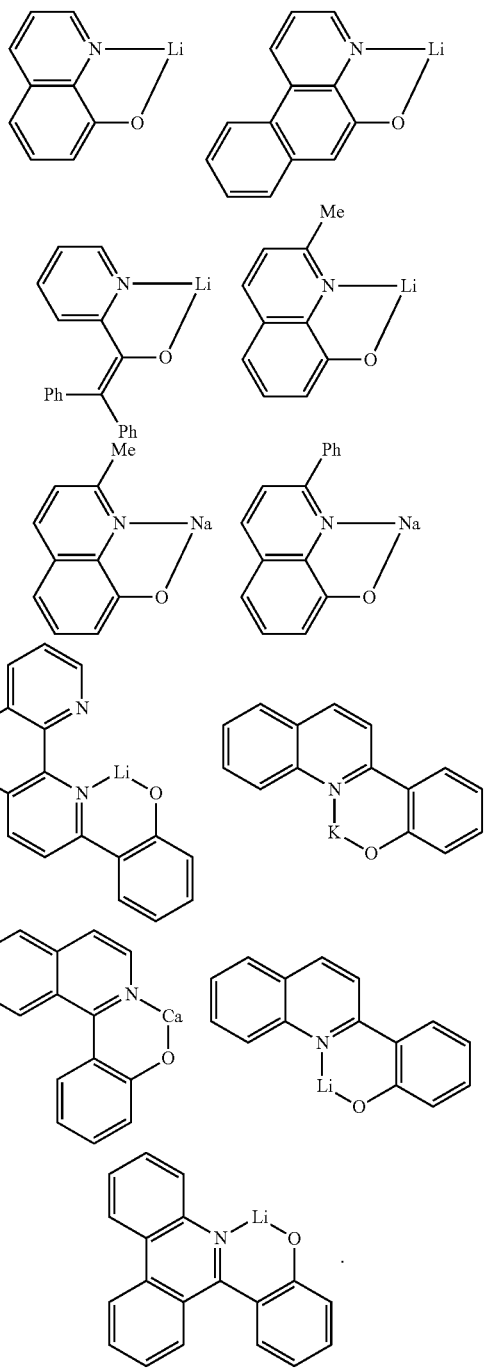

* * * * *

UNITED STATES PATENT AND TRADEMARK OFFICE
CERTIFICATE OF CORRECTION

PATENT NO. : 11,877,510 B2
APPLICATION NO. : 17/064409
DATED : January 16, 2024
INVENTOR(S) : Jang et al.

It is certified that error appears in the above-identified patent and that said Letters Patent is hereby corrected as shown below:

In the Claims

In Claim 3, at Column 72, the following text should be inserted at Line 57:
-- moiety is any one selected from among the following structures: --

In Claim 3, at Column 73, the following text at Lines 43-44 should be deleted:
"moiety is any one selected from among the following structures:"

Signed and Sealed this
Seventh Day of May, 2024

Katherine Kelly Vidal
*Director of the United States Patent and Trademark Office*